(12) United States Patent
Hayami et al.

(10) Patent No.: US 11,656,451 B2
(45) Date of Patent: May 23, 2023

(54) IMAGE PROCESSING APPARATUS FOR ENDOSCOPE, IMAGE PROCESSING METHOD FOR ENDOSCOPE, AND RECORDING MEDIUM

(71) Applicant: OLYMPUS CORPORATION, Tokyo (JP)

(72) Inventors: Takehito Hayami, Tokyo (JP); Yamato Kanda, Hino (JP); Makoto Kitamura, Hachioji (JP); Akihiro Kubota, Kokubunji (JP)

(73) Assignee: OLYMPUS CORPORATION, Tokyo (JP)

( * ) Notice: Subject to any disclaimer, the term of this patent is extended or adjusted under 35 U.S.C. 154(b) by 5 days.

(21) Appl. No.: 17/140,609

(22) Filed: Jan. 4, 2021

(65) Prior Publication Data
US 2021/0149182 A1 May 20, 2021

Related U.S. Application Data

(63) Continuation of application No. PCT/JP2018/025791, filed on Jul. 6, 2018.

(51) Int. Cl.
*G02B 23/24* (2006.01)
*G06T 7/00* (2017.01)

(52) U.S. Cl.
CPC ..... *G02B 23/2446* (2013.01); *G02B 23/2484* (2013.01); *G06T 7/0012* (2013.01); *G06T 2207/10068* (2013.01)

(58) Field of Classification Search
CPC ............ G02B 23/2446; G02B 23/2484; G06T 7/0012; G06T 2207/10068;
(Continued)

(56) References Cited

U.S. PATENT DOCUMENTS

2005/0152588 A1* 7/2005 Yoshida .................. G06T 15/08
600/407
2009/0074268 A1 3/2009 Tanaka et al.
(Continued)

FOREIGN PATENT DOCUMENTS

EP 1994879 A1 11/2008
EP 2517614 A1 10/2012
(Continued)

OTHER PUBLICATIONS

International Search Report dated Oct. 2, 2018 issued in PCT/JP2018/025791.

*Primary Examiner* — Maria E Vazquez Colon
(74) *Attorney, Agent, or Firm* — Scully, Scott, Murphy & Presser, P.C.

(57) ABSTRACT

An image processing apparatus for endoscope includes a processor. The processor sequentially receives a plurality of observation images of an endoscope, detects one or more lesioned parts from each of the plurality of observation images, analyzes visibility of at least one of a distance from the endoscope, an occupied area, a shape, a size, a position in the observation image, a color, luminance, or an organ part relating to the detected lesioned part, sets a display extension time of a detection result of the lesioned part according to the visibility, and outputs the observation image to which the detection result of the lesioned part is added.

27 Claims, 10 Drawing Sheets

(58) Field of Classification Search
CPC . G06T 2207/10016; G06T 2207/30096; G06T 2207/30168; G06T 2200/24; A61B 1/045
See application file for complete search history.

(56) References Cited

U.S. PATENT DOCUMENTS

| | | | | |
|---|---|---|---|---|
| 2010/0092055 | A1* | 4/2010 | Matsuda | A61B 1/00009 382/128 |
| 2012/0274754 | A1* | 11/2012 | Tsuruoka | A61B 1/00045 348/222.1 |
| 2014/0044421 | A1* | 2/2014 | Sasaki | G11B 27/34 386/343 |
| 2014/0046131 | A1* | 2/2014 | Morita | A61B 1/06 600/109 |
| 2015/0181185 | A1 | 6/2015 | Ikemoto et al. | |
| 2016/0379363 | A1* | 12/2016 | Kitamura | A61B 1/04 600/371 |
| 2019/0069757 | A1* | 3/2019 | Iwaki | A61B 1/000094 |
| 2019/0114738 | A1* | 4/2019 | Sonoda | A61B 1/00009 |
| 2020/0258224 | A1* | 8/2020 | Endo | G16H 30/40 |
| 2020/0306516 | A1* | 10/2020 | Jones | A61K 47/10 |

FOREIGN PATENT DOCUMENTS

| | | | | |
|---|---|---|---|---|
| EP | 2875775 | A1 | 5/2015 | |
| JP | 2007-244518 | A | 9/2007 | |
| JP | 2009-105705 | A | 5/2009 | |
| JP | 2014-018333 | A | 2/2014 | |
| WO | WO-2006124648 | A2 * | 11/2006 | A61B 1/00186 |
| WO | WO 2007/105516 | A1 | 9/2007 | |
| WO | WO 2011/096279 | A1 | 8/2011 | |
| WO | WO 2014/013777 | A1 | 1/2014 | |
| WO | WO 2015/137016 | A1 | 9/2015 | |
| WO | WO 2017/104192 | A1 | 6/2017 | |
| WO | WO-2017203560 | A1 * | 11/2017 | A61B 1/00009 |

* cited by examiner

IMAGE PROCESSING APPARATUS FOR ENDOSCOPE, IMAGE PROCESSING METHOD FOR ENDOSCOPE, AND RECORDING MEDIUM

CROSS REFERENCE TO RELATED APPLICATION

This application is a continuation application of PCT/JP2018/025791 filed on Jul. 6, 2018, the entire contents of which are incorporated herein by this reference.

BACKGROUND OF THE INVENTION

1. Field of the Invention

The present invention relates to an image processing apparatus for endoscope, an image processing method for endoscope, and a recording medium.

2. Description of the Related Art

Endoscopes have been widely used in the medical field and the industrial field. For example, in the medical field, a surgeon can find and identify a lesioned part by viewing an endoscope image of an inside of a subject displayed on a display apparatus and perform treatment on the lesioned part using a treatment instrument.

An image processing apparatus that adds highlighted display by a marker such as a frame to a lesioned part detected from an endoscopic image and displays the lesioned part in order to prevent a surgeon from overlooking the lesioned part when viewing an endoscopic image has been generally well known.

Incidentally, in an endoscopic observation, since relative positions of an object in a body cavity, an image of which is picked up by an endoscope, and an insertion section of the endoscope inserted into the body cavity can always change, it is difficult to correctly detect, in all frames, a lesioned part once detected. Therefore, a method of performing, for a frame in which the lesioned part is not detected, extended display of a marker or the like using information concerning a nearest frame in which the lesioned part is detected is conceivable.

For example, it is possible to realize the extended display of the marker or the like by applying, to an image processing apparatus for endoscopic image, a method of performing, for a general image, extended display of display information, proposed in Japanese Patent Application Laid-Open Publication No. 2009-105705.

SUMMARY OF THE INVENTION

An image processing apparatus for endoscope according to an aspect of the present invention includes a processor. The processor sequentially receives a plurality of observation images obtained by picking up an image of an object with an endoscope; detects one or more lesioned parts, which each is an observation target of the endoscope, from each of the plurality of observation images; analyzes visibility of at least one of a distance from the endoscope, an occupied area, a shape, a size, a position in each of the observation images, a color, luminance, or an organ part relating to each of the detected lesioned parts; sets a display extension time of a detection result of each of the lesioned parts according to the analyzed visibility; and outputs each of the observation images to which the detection result of the lesioned parts is added.

An image processing method for endoscope according to an aspect of the present invention includes: sequentially receiving a plurality of observation images obtained by picking up an image of an object with an endoscope; detecting one or more lesioned parts, which each is an observation target of the endoscope, from each of the plurality of observation images; analyzing visibility of at least one of a distance from the endoscope, an occupied area, a shape, a size, a position in each of the observation images, a color, luminance, or an organ part relating to each of the detected lesioned parts; setting a display extension time of a detection result of each of the lesioned parts according to the analyzed visibility; and outputting each of the observation images to which the detection result of the lesioned parts is added.

A recording medium according to an aspect of the present invention is a computer-readable non-transitory recording medium that stores a computer program, the computer program causing the computer to: sequentially acquire a plurality of observation images obtained by picking up an image of an object with an endoscope; detect one or more lesioned parts, which each is an observation target of the endoscope, from each of the plurality of observation images; analyze visibility of at least one of a distance from the endoscope, an occupied area, a shape, a size, a position in each of the observation images, a color, luminance, or an organ part relating to each of the detected lesioned parts; set a display extension time of a detection result of each of the lesioned parts according to the analyzed visibility; and output each of the observation images to which the detection result of the lesioned parts is added.

DETAILED DESCRIPTION OF THE PREFERRED EMBODIMENTS

Embodiments of the present invention are explained below with reference to the drawings.

First Embodiment

Figure 1:
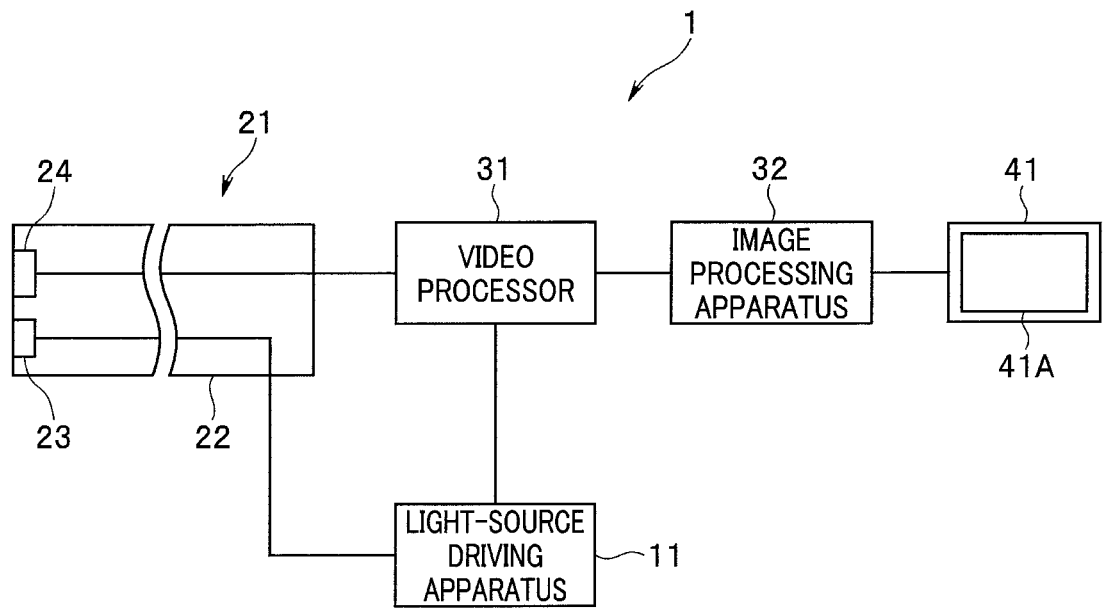
FIG. 1 is a diagram showing a configuration of a main part of an endoscope system including an image processing apparatus according to a first embodiment.

FIG. 1 is a diagram showing a configuration of a main part of an endoscope system including an image processing apparatus according to a first embodiment. An endoscope system 1 includes, as shown in FIG. 1, a light-source driving apparatus 11, an endoscope 21, a video processor 31, an image processing apparatus for endoscope (hereinafter referred to as image processing apparatus) 32, and a display apparatus 41.

The light-source driving apparatus 11 includes, for example, a drive circuit. The light-source driving apparatus 11 is connected to the endoscope 21 and the video processor 31. The light-source driving apparatus 11 is configured to generate, based on a light source control signal from the video processor 31, a light source driving signal for driving a light source section 23 of the endoscope 21 and output the generated light source driving signal to the endoscope 21.

The endoscope 21 is connected to the light-source driving apparatus 11 and the video processor 31. The endoscope 21 includes an elongated-shaped insertion section 22 insertable into a body cavity of a subject. The light source section 23 and an image pickup section 24 are provided at a distal end portion of the insertion section 22.

The light source section 23 includes a light emitting element such as a white LED. The light source section 23 is configured to generate illumination light by emitting light according to the light source driving signal outputted from the light-source driving apparatus 11 and emit the generated illumination light to an object such as a biological tissue.

The image pickup section 24 includes an image sensor such as a color CCD or a color CMOS. The image pickup section 24 is configured to perform operation corresponding to an image pickup control signal outputted from the video processor 31. The image pickup section 24 is configured to receive reflected light from the object illuminated by the illumination light from the light source section 23, pick up an image of the received reflected light to generate an image pickup signal, and output the generated image pickup signal to the video processor 31.

The video processor 31 is connected to the light-source driving apparatus 11 and the endoscope 21. The video processor 31 is configured to generate a light source control signal for controlling a light emission state of the light source section 23 and output the light source control signal to the light-source driving apparatus 11. The video processor 31 is configured to generate an image pickup control signal for controlling an image pickup operation of the image pickup section 24 and output the image pickup control signal. The video processor 31 is configured to generate an observation image G1 of an object by applying predetermined processing to an image pickup signal outputted from the endoscope 21 and sequentially output the generated observation image G1 to the image processing apparatus 32 frame by frame.

Figure 2:
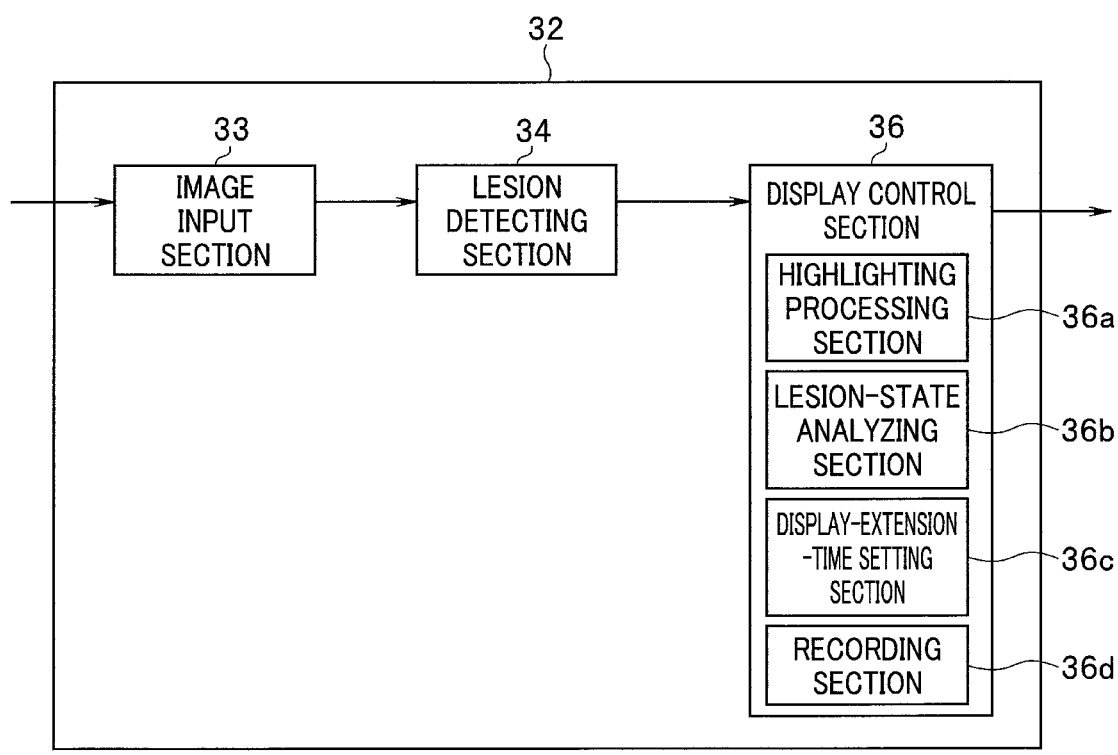
FIG. 2 is a block diagram for explaining an example of a configuration relating to image processing of the image processing apparatus according to the first embodiment.

The image processing apparatus 32 includes an electronic circuit such as an image processing circuit. The image processing apparatus 32 is configured to perform operation for generating an image for display based on the observation image G1 outputted from the video processor 31 and causing the display apparatus 41 to display the generated image for display. The image processing apparatus 32 includes, as shown in FIG. 2, an image input section 33, a lesion detecting section 34, and a display control section 36. FIG. 2 is a block diagram for explaining an example of a configuration relating to image processing of the image processing apparatus according to the first embodiment.

Note that the image processing apparatus 32 is not limited to be configured by the processor including the electronic circuit such as the image processing circuit. For example, the image processing apparatus 32 may be configured to serve functions of the respective sections in the image processing apparatus 32 by causing a processor including a CPU to execute software. The image processing apparatus 32 may be configured by a processor including an integrated circuit such as an FPGA (field programmable gate array) including circuit sections corresponding to the respective sections in the image processing apparatus 32. A computer program to be executed by a computer (software to be executed by a processor) is recorded in a computer-readable non-transitory recording medium.

The image input section 33 outputs the observation image G1 received from the video processor 31 to the lesion detecting section 34.

The lesion detecting section 34 is configured to detect a lesion region Ln (n=1, 2, . . . ) included in the observation image G1 sequentially outputted from the image input section 33. The lesion detecting section 34 detects the lesion region Ln from the observation image G1 by performing processing for applying, to the observation image G1, an image identifier that acquires, in advance, a function capable of identifying a polyp image with a learning method such as deep learning. Note that the detection of the lesion region Ln is not limited to the learning method described above and other methods may be used. For example, polyp candidate detection processing disclosed in Japanese Patent Application Laid-Open Publication No. 2007-244518 may be used.

The display control section 36 functioning as a display-control output section is connected to the display apparatus 41. The display control section 36 includes a highlighting processing section 36a, a lesion-state analyzing section 36b, a display-extension-time setting section 36c, and a recording section 36d. The display control section 36 is configured to perform processing for generating an image for display using the observation image G1 sequentially outputted from the video processor 31 and perform processing for causing a display screen 41A of the display apparatus 41 to display the generated image for display.

In order to highlight a position of the lesion region Ln detected by the lesion detecting section 34, the highlighting processing section 36a performs highlighting processing for generating a marker image G2 surrounding the lesion region Ln and adding the marker image G2 to the observation image G1. The highlighting processing is started from a point in time when the lesion region Ln is detected. The highlighting processing ends when a display extension time set by the display-extension-time setting section 36c elapses after the detection of the lesion region Ln is interrupted. Note that the interruption includes a case in which the lesion region Ln moves to an outside of a screen after the lesion region Ln is detected and a case in which the lesion detecting section 34 fails in the detection of the lesion region Ln.

Note that the marker image G2 added by the highlighting processing of the highlighting processing section 36a may have any form as long as the marker image G2 is capable of presenting the position of the lesion region Ln as visual information. The marker image G2 may be any image having, for example, a square shape, a triangular shape, a circular shape, and a star shape. The marker image G2 may be an image not surrounding the lesion region Ln if the image can indicate the position of the lesion region Ln. For example, the position of the lesion region Ln may be indicated by differentiating brightness and a color tone of the lesion region Ln from brightness and a color tone of a peripheral region. Further, presence of a lesion region may be indicated by generating a message indicating the lesion region as support information and displaying the message in a form of a popup message or the like in a vicinity of the lesion region, a periphery of an observation image, or the like or generating and displaying a flag.

The lesion-state analyzing section 36b analyzes a state of the lesion region Ln detected by the lesion detecting section 34. A result of the analysis is outputted to the display-extension-time setting section 36c.

The display-extension-time setting section 36c sets, based on the analysis result of the state of the lesion region Ln, a display extension time for the marker image G2 generated by the highlighting processing section 36a. Note that the display extension time set by the display-extension-time setting section 36c means a time period in which the marker image G2 additionally displayed in the observation image G1 is displayed in the image for display even after the detection of the lesion region Ln is interrupted. Two or more kinds of display extension times are set in advance in the display-extension-time setting section 36c. An appropriate display extension time is selected according to an analysis result received from the lesion-state analyzing section 36b.

The display extension time is specified according to the number of frames. For example, one frame is set in advance as a first display extension time and ten frames are set in advance as a second display extension time. When the number of frames per one second is thirty, the first display extension time is approximately 0.03 seconds and the second display extension time is approximately 0.33 seconds.

In a state in which the lesion region Ln is less easily seen as a result of analyzing the state of the lesion region Ln or when malignancy is high, the second display extension time is selected in order to prevent the surgeon from overlooking a lesioned part. On the other hand, in a state in which the lesion region Ln is easily seen or when malignancy is low, the first display extension time is selected in order to improve visibility.

The recording section 36d is configured to sequentially record (in time series), as a plurality of recorded images R1, a plurality of observation images G1 sequentially outputted from the video processor 31. Note that the recording section 36d may also function as a computer-readable non-transitory recording medium that stores a computer program.

The display apparatus 41 includes a monitor or the like and is configured to be able to display an image for display outputted from the image processing apparatus 32.

Figure 3:
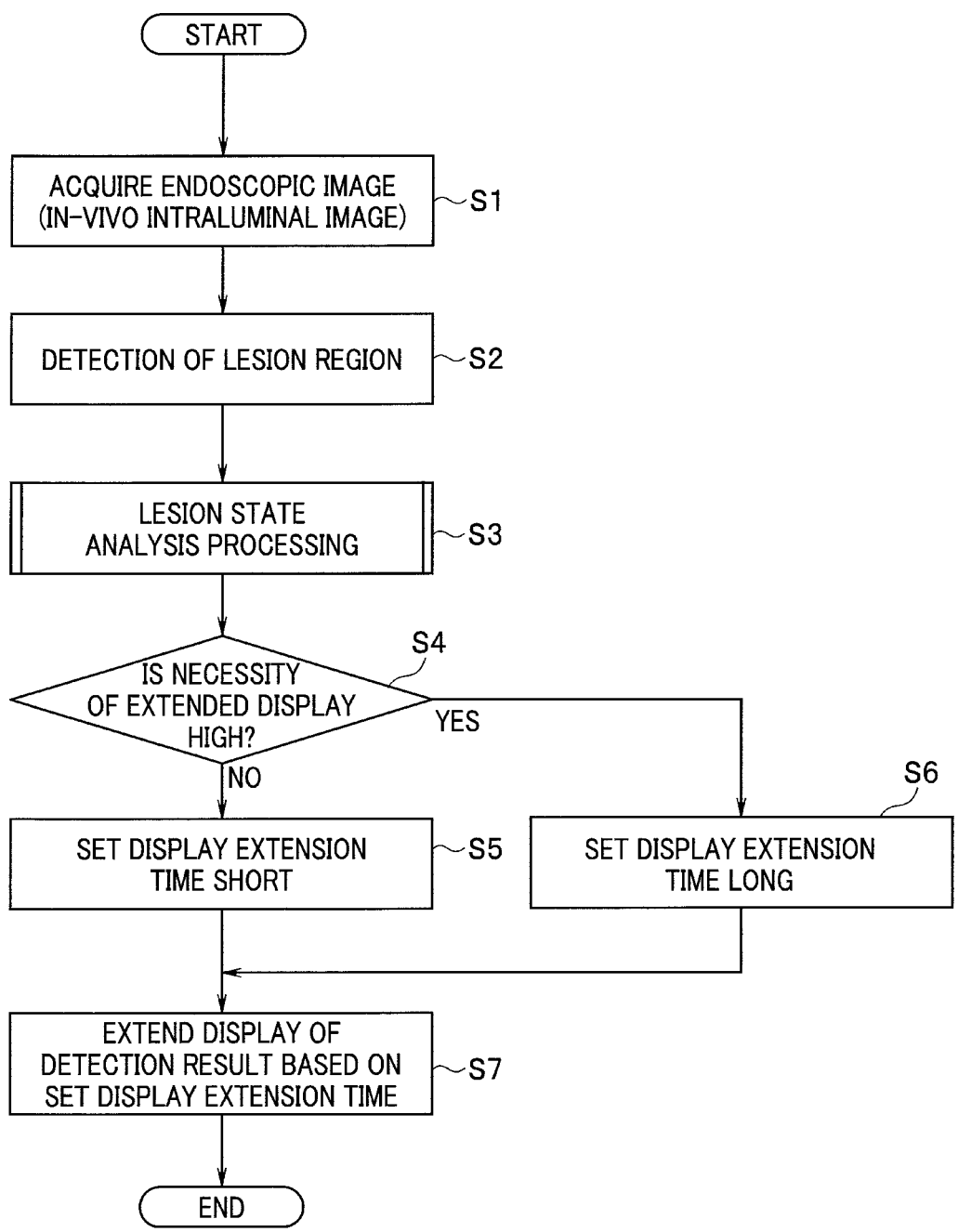
FIG. 3 is a flowchart showing an example of processing performed in the image processing apparatus according to the first embodiment.

Subsequently, action of the present embodiment is explained. FIG. 3 is a flowchart showing an example of processing performed in the image processing apparatus according to the first embodiment. Note that the computer program recorded in the recording medium may be a program for performing processing shown in FIG. 3 (and FIG. 10 to FIG. 13 referred to below).

For example, when power supplies of the light-source driving apparatus 11 and the video processor 31 are turned on, the endoscope 21 emits illumination light to an object, receives reflected light from the object, picks up an image of the received reflected light to generate an image pickup signal, and outputs the generated image pickup signal to the video processor 31.

The video processor 31 generates the observation image G1 of the object by applying predetermined processing to the image pickup signal outputted from the endoscope 21 and sequentially outputs the generated observation image G1 to the image processing apparatus 32 frame by frame. In other words, the image input section 33 acquires an endoscopic image (the observation image G1), which is an in-vivo intraluminal image, from the video processor 31 (S1). The image input section 33 outputs the acquired image to the lesion detecting section 34.

The lesion detecting section 34 detects the lesion region Ln from the observation image G1 by performing processing for applying, to the observation image G1, an image identifier that acquires, in advance, a function capable of identifying a polyp image with a learning method such as deep learning (S2). A detection result of the lesion region Ln is outputted to the display control section 36.

In the display control section 36, the lesion-state analyzing section 36b analyzes a state of the lesion region Ln. The lesion-state analyzing section 36b determines importance (malignancy or the like), a position, and the like of the lesion region Ln with an image analysis and evaluates, for example, possibility of overlooking (S3). The display-extension-time setting section 36c receives an analysis result of the state of the lesion region Ln.

Subsequently, the display-extension-time setting section 36c sets, based on the analysis result of the state of the lesion region Ln, a display extension time for the marker image G2 added to the display screen in order to highlight the lesion region Ln (S4). In a state in which the lesion region Ln is less easily seen or when malignancy is high (S4, YES), the processing proceeds to S6 and the display-extension-time setting section 36c sets the display extension time long. On the other hand, in a state in which the lesion region Ln is easily seen or when malignancy is low (S4, NO), the processing proceeds to S5 and the display-extension-time setting section 36c sets the display extension time short.

When the setting of the display extension time ends according to the processing of S5 or S6, the processing proceeds to processing of S7. In S7, the highlighting processing section 36a performs highlighting processing for generating the marker image G2 surrounding the lesion region Ln and adding the marker image G2 to the observation image G1. The highlighting processing is started from a point in time when the lesion region Ln is detected and ends at a point in time when the display extension time elapses after the detection of the lesion region Ln is interrupted because the lesion region Ln moves to an outside of a screen or the lesion detecting section 34 fails in the detection. The display control section 36 outputs an image obtained by adding the marker image G2 to the observation image G1 according to necessity to the display apparatus 41 as an image for display and ends a series of processing.

Figure 4:
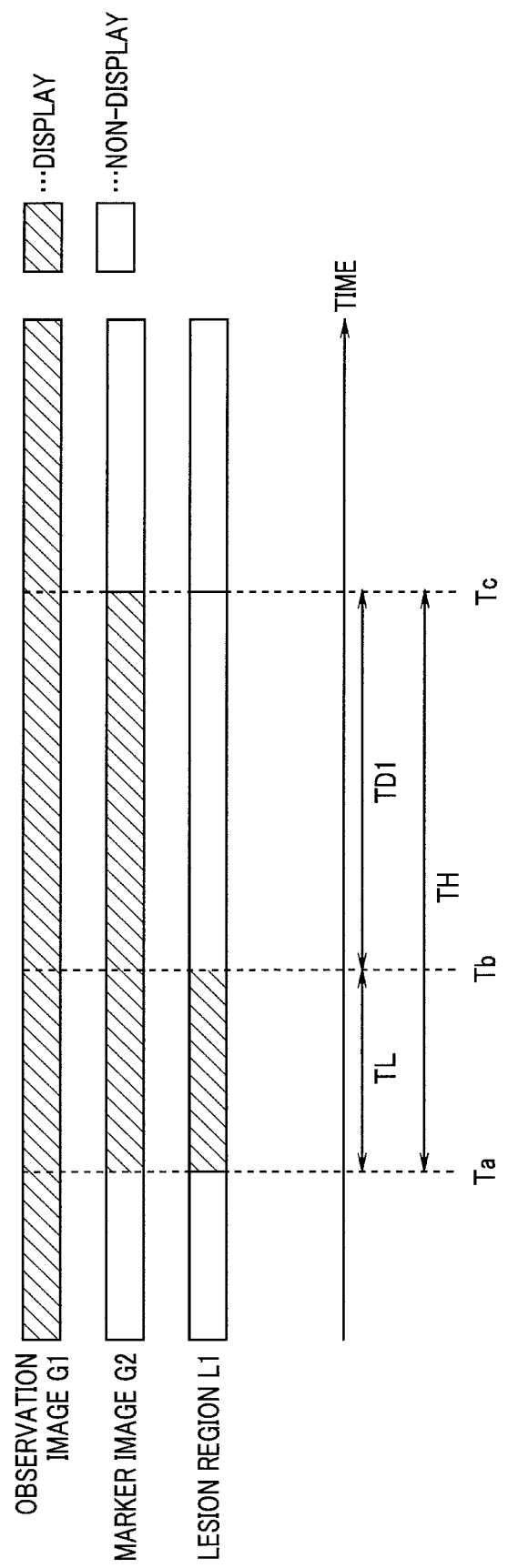
FIG. 4 is a time chart for explaining an example of processing performed in the image processing apparatus according to the first embodiment.
Figure 5:
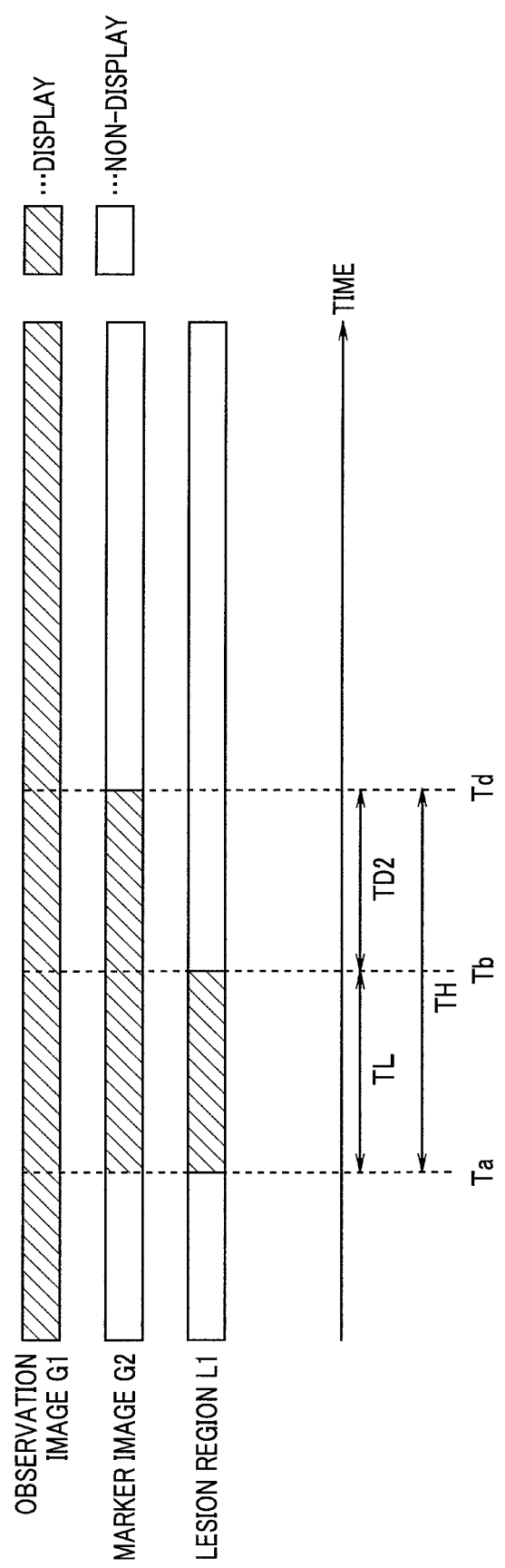
FIG. 5 is a time chart for explaining another example of the processing performed in the image processing apparatus according to the first embodiment.
Figure 6:
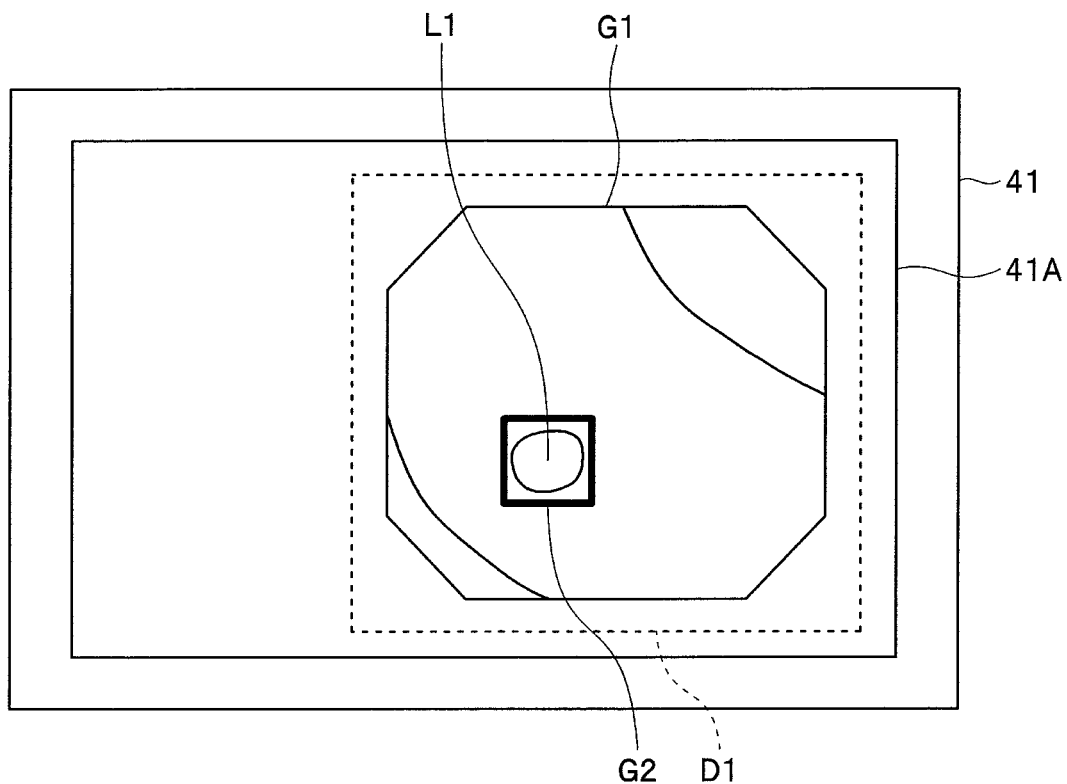
FIG. 6 is a diagram showing an example of an image for display displayed on a display apparatus through processing of the image processing apparatus according to the first embodiment.

FIG. 4 and FIG. 5 are time charts for explaining an example of processing performed in the image processing apparatus according to the present embodiment. FIG. 4 is a time chart in a state in which the lesion region Ln is less easily seen or in a case in which malignancy is high. FIG. 5 is a time chart in a state in which the lesion region Ln is easily seen or a case in which malignancy is low. FIG. 6 is a diagram showing an example of an image for display displayed on the display apparatus through processing of the image processing apparatus according to the present embodiment.

At timing (=time point Ta) when detection of a lesion region L1 by the lesion detecting section 34 is started, the display control section 36 performs processing for causing the display apparatus 41 to display an image for display in which the observation image G1 obtained by adding the marker image G2 to the lesion region L1 is arranged in a display region D1 of the display screen 41A. With such operation of the display control section 36, for example, in a period of time Ta to Tb shown in FIG. 4 and FIG. 5, an image for display shown in FIG. 6 is displayed on the display screen 41A of the display apparatus 41.

The display control section 36 continues the addition of the marker image G2 to the observation image G1 in a period from timing (=time point Tb) when the detection of the lesion region L1 by the lesion detecting section 34 is interrupted to timing (=time point Tc or Td) when the display extension time elapses.

In other words, in a time period TL in which the lesion detecting section 34 continues the detection of the lesion region L1, the image for display in the state in which the marker image G2 is added to the observation image G1 is generated and displayed irrespective of a state of the lesion region Ln. After the timing when the detection of the lesion region L1 is interrupted, an addition time of the marker image G2 changes according to the state of the lesion region Ln.

In other words, in a state in which the lesion region Ln is less easily seen or when malignancy is high, the image for display in the state in which the marker image G2 is added to the observation image G1 is generated and displayed on the display screen 41A of the display apparatus 41 in a display extension time TD1 from the timing when the detection of the lesion region L1 is interrupted. On the other hand, in a state in which the lesion region Ln is easily seen or when malignancy is low, the image for display in the state in which the marker image G2 is added to the observation image G1 is generated and displayed on the display screen 41A of the display apparatus 41 in a display extension time TD2 (TD2<TD1) from the timing when the detection of the lesion region L1 is interrupted.

In this way, according to the embodiment explained above, by adjusting, according to a state of the legion region Ln, a time period (a display extension time) in which the marker image G2 is continuously displayed after the detection of the lesion region Ln is interrupted, it is possible to reduce overlooking of a lesioned part that could occur in an endoscopic observation and improve visibility.

Note that although the appropriate display extension time is selected out of the two kinds of times TD1 and TD2 set in advance in the above explanation, the appropriate display extension time may be selected out of three or more kinds of display extension times according to the state of the lesion region Ln.

Although the image for display includes the observation image G1, which is a movie, in the above explanation, the image for display may be formed by the observation image G1 and the recorded image R1, which is a still image.

Figure 7:
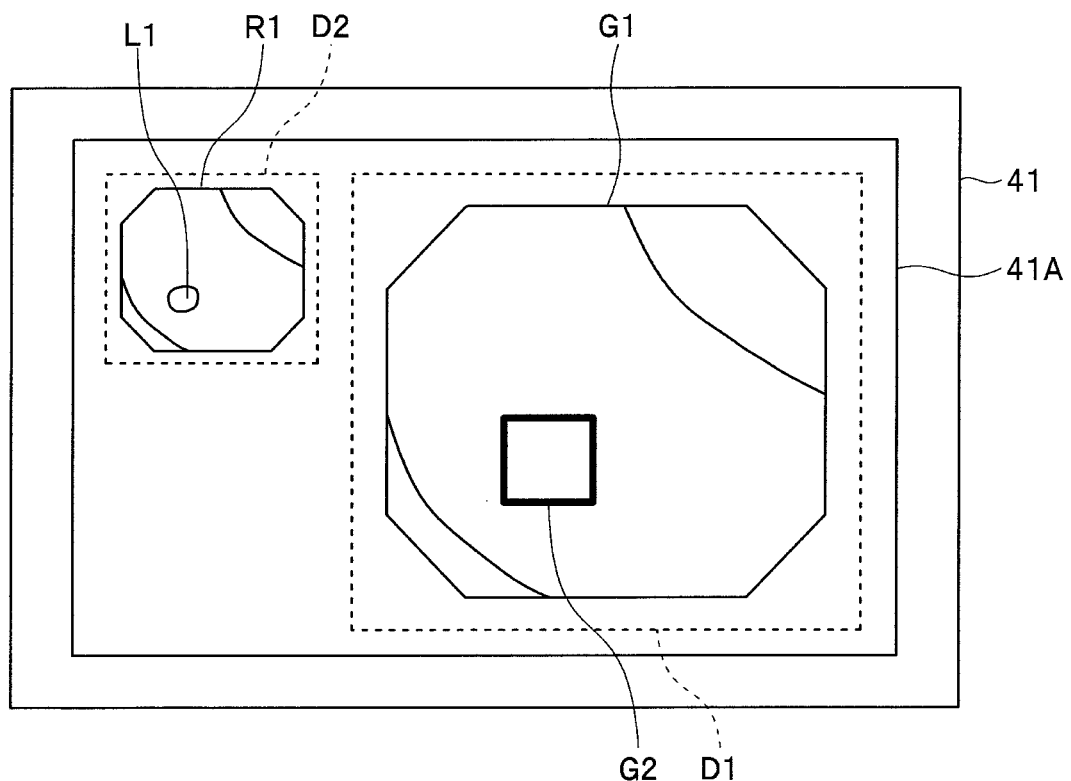
FIG. 7 is a diagram showing another example of the image for display displayed on the display apparatus through the processing of the image processing apparatus according to the first embodiment.

FIG. 7 is a diagram showing another example of the image for display displayed on the display apparatus through the processing of the image processing apparatus according to the present embodiment. When the detection of the lesion region L1 is interrupted, the display control section 36 starts, at timing when the detection of a lesion region L1 by a lesion-candidate detecting section 34b is interrupted, processing for causing the display apparatus 41 to display an image for display in which the observation image G1 is arranged in the display region D1 of the display screen 41A and the recorded image R1 recorded by the recording section 36d during the detection of the lesion region L1 is arranged in a display region D2 of the display screen 41A. At timing when the display extension time elapses from the timing when the detection of the lesion region L1 is interrupted, the display control section 36 ends the processing for arranging the recorded image R1 in the display region D2 of the display screen 41A.

With such operation of the display control section 36, for example, until the display extension time elapses after the timing (=time point Tb) when the detection of the lesion region L1 is interrupted, the image for display in which the recorded image R1 equivalent to the observation image G1 shown in FIG. 6 is arranged in the display region D2 is displayed on the display screen 41A of the display apparatus 41. Note that it is assumed that, for example, the display region D2 is set in advance as a region having a size smaller than the display region D1 on the display screen 41A.

In other words, by indicating the position of the lesion region Ln to the surgeon even after the detection of the lesion region L1 is interrupted using a sub-screen as explained above, it is possible to further reduce overlooking of a lesioned part while preventing deterioration in visibility for the observation image G1.

Figure 8:
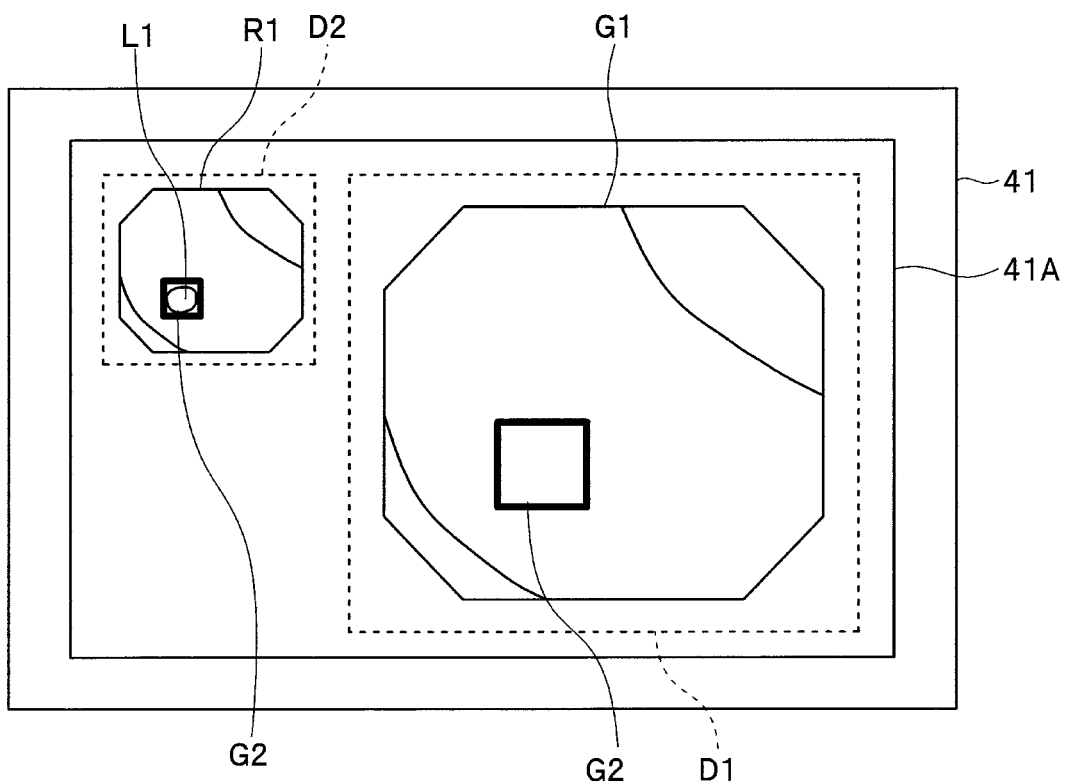
FIG. 8 is a diagram showing still another example of the image for display displayed on the display apparatus through the processing of the image processing apparatus according to the first embodiment.

As shown in FIG. 8, in the display region D2 of the display screen 41A, not only the recorded image R1 but also the marker image G2 may be added to the lesion region L1 of the image and displayed. FIG. 8 is a diagram showing still another example of the image for display displayed on the display apparatus through the processing of the image processing apparatus according to the present embodiment. By applying the highlighting processing and adding the marker image G2 to the recorded image R1 as well and displaying the recorded image R1, the position of the lesioned part is more easily identified. It is possible to further reduce overlooking.

Second Embodiment

In the first embodiment explained above, the time period (the display extension time) in which the marker image G2 is continuously displayed after the detection of the lesion region Ln is interrupted is adjusted according to the state of the lesion region Ln. However, in the present embodiment, visibility of the lesion region Ln is analyzed and a display extension time is determined based on a result of the analysis.

An image processing apparatus in the present embodiment has the same configuration as the configuration of the image processing apparatus 32 in the first embodiment. The same components are denoted by the same reference numerals and signs and explanation of the components is omitted.

Figure 9:
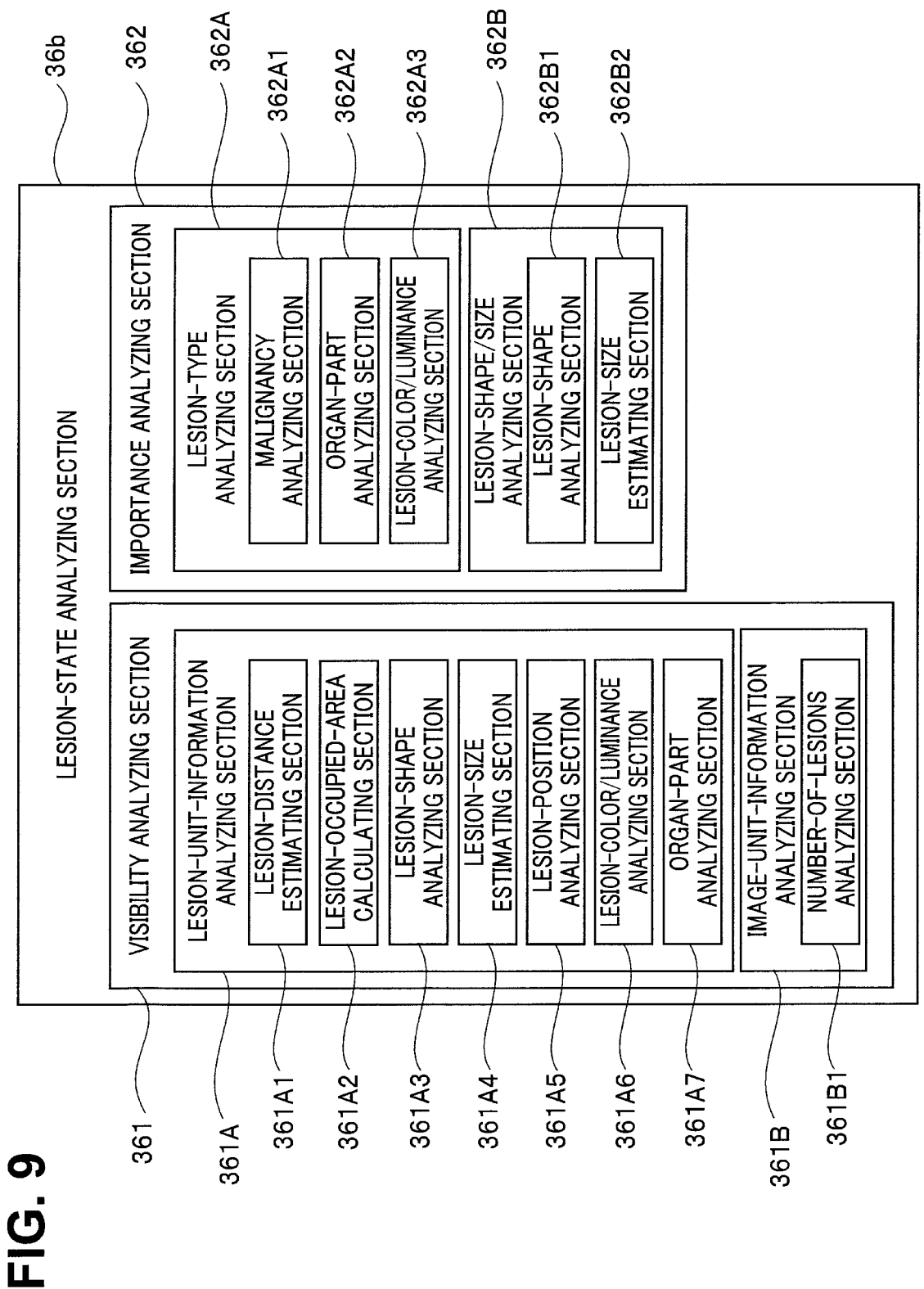
FIG. 9 is a block diagram for explaining an example of a configuration of a lesion-state analyzing section according to a second embodiment.

FIG. 9 is a block diagram for explaining an example of a configuration of a lesion-state analyzing section according to the second embodiment. Note that FIG. 9 shows not only a configuration according to the present embodiment explained below but also a configuration according to a third embodiment explained after the present embodiment. Operations of respective sections are explained in detail in corresponding parts of the following explanation.

Figure 10:
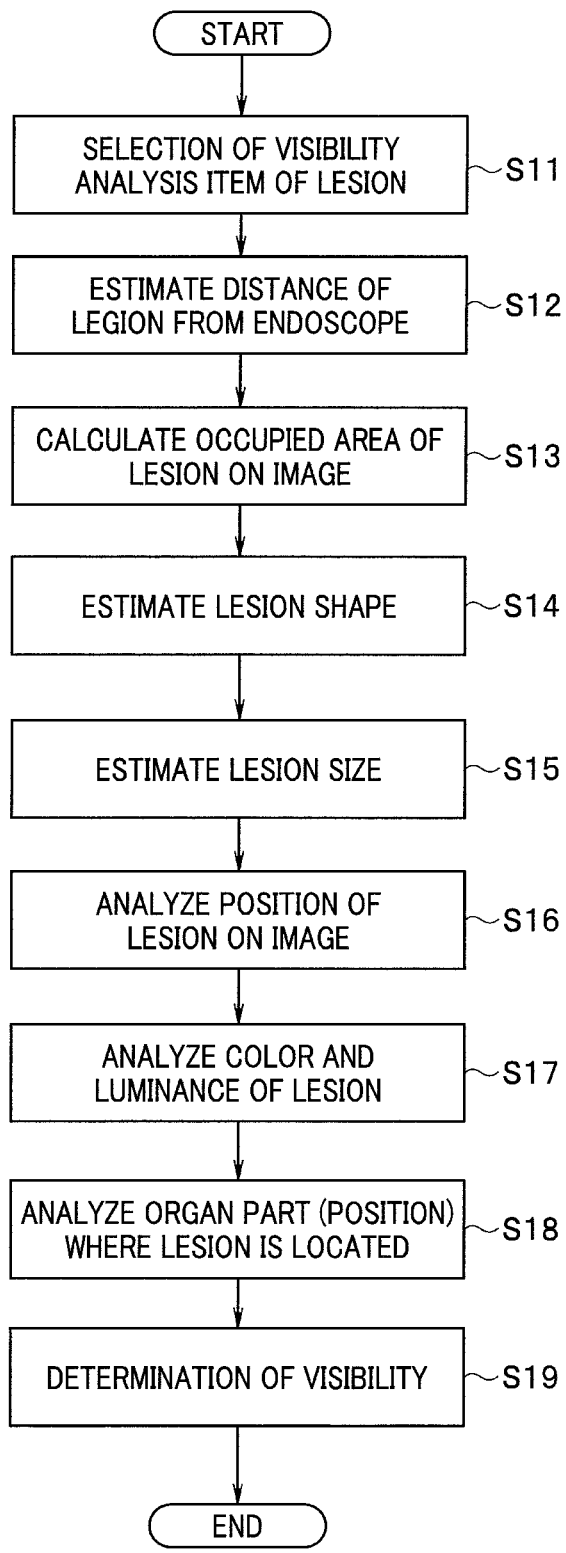
FIG. 10 is a flowchart showing an example of a flow of lesion analysis processing according to the second embodiment.

FIG. 10 is a flowchart showing an example of a flow of lesion analysis processing according to the second embodiment. A visibility analyzing section 361, in particular, a lesion-unit-information analyzing section 361A in the lesion-state analyzing section 36b in FIG. 9 relates to processing shown in FIG. 10.

The lesion-state analyzing section 36b analyzes the visibility of the lesion region Ln. First, the lesion-state analyzing section 36b selects an item for which an analysis of visibility is performed (S11). Examples of analysis items of visibility include items such as (a) a distance between the endoscope 21 and the lesion region Ln, (b) a ratio of an occupied area of the lesion region Ln in the observation image G1, (c) a shape of the lesion region Ln, (d) a size of the lesion region Ln, (e) a position of the lesion region Ln in the observation image G1, (f) a color and luminance of the lesion region Ln, and (g) an organ part where the lesion region Ln is located. The lesion-state analyzing section 36b performs an analysis about an item selected out of these items. Note that the analysis of visibility may be performed by selecting only one item or may be performed by selecting a plurality of items.

(a) Distance Between Endoscope 21 and Lesion Region Ln

When this item is selected as the analysis item, processing (S12) explained below is performed. A lesion-distance estimating section 361A1 shown in FIG. 9 relates to the processing of S12.

The lesion-distance estimating section 361A1 estimates image pickup distances to respective pixels in an image. Among publicly-known various techniques, photographing distance estimation performed assuming that a photographing target is a uniform diffuser based on an image is explained.

More specifically, first, as a low absorption wavelength component, a low absorption wavelength (for example, red (R) wavelength) component having a lowest degree of absorption or diffusion in an organism is selected. This is to reduce a pixel value decrease due to a blood vessel or the like reflected on a mucosal surface and obtain pixel value information most correlating to an image pickup distance to the mucosal surface and is because, in an image formed by three components of red (R), green (G), and blue (B), the red (R) component is a component of a wavelength separating from a blood absorption band and of a long wavelength and is less easily affected by the absorption or the diffusion in the organism. The red (R) component is selected.

The lesion-distance estimating section 361A1 estimates an image pickup distance obtained by assuming a uniform diffuser based on a pixel value of the low absorption wavelength component. More specifically, the image pickup distance is calculated by the following Equation (1).

[Equation 1]

$$r = \sqrt{\frac{I \times K \times \cos\theta}{L}} \quad \text{(1) Equation}$$

where, r indicates the image pickup distance, I indicates radiation intensity of a light source obtained by measurement beforehand, and K indicates a diffusion reflection coefficient of the mucosal surface, which is an average value, measured beforehand. θ indicates an angle formed by a normal vector of the mucosal surface and a vector from the surface to a light source and is a value determined by a positional relation between a light source in an insertion section distal end portion of the endoscope 21 and the mucosal surface. An average value is set as θ beforehand. L indicates an R component value of a pixel on which the mucosal surface of the image pickup distance estimation target is reflected.

Note that before the image pickup distance estimation, correction of pixel value unevenness due to an optical system and an illumination system, which could be accuracy deterioration factors of respective kinds of processing, and exclusion of non-mucous regions such as specular reflection, residues, and bubbles may be performed.

A method based on an image is explained above. Besides, the image pickup distance may be calculated based on a range finding sensor or the like.

As explained above, the lesion-distance estimating section 361A1 estimates the distance between the endoscope 21 and the lesion region Ln and outputs the distance as the analysis result.

(b) Ratio of Occupied Area of Lesion Region Ln in Observation Image G1.

When this items is selected as the analysis item, processing (S13) explained below is performed. A lesion-occupied-area calculating section 361A2 in FIG. 9 relates to the processing of S13.

The lesion-occupied-area calculating section 361A2 calculates a ratio of an area occupied by the lesion region Ln in the observation image G1. More specifically, the lesion-occupied-area calculating section 361A2 detects the lesion region Ln from the observation image G1 by performing processing for applying, to the observation image G1, an image identifier that acquires, in advance, a function capable of identifying a polyp image with a learning method such as deep learning. The lesion-occupied-area calculating section 361A2 calculates the number of pixels included in the lesion region Ln. Finally, the lesion-occupied-area calculating section 361A2 calculates an occupied area ratio by dividing the number of pixels included in the legion region Ln by a total number of pixels forming the observation image G1.

Note that position information of the lesion region Ln may be acquired from the lesion detecting section 34. The detection of the lesion region Ln is not limited to the learning method described above and other methods may be used. For example, polyp candidate detection processing disclosed in Japanese Patent Application Laid-Open Publication No. 2007-244518 may be used.

As explained above, the lesion-occupied-area calculating section 361A2 calculates the ratio of the occupied area of the lesion region Ln in the observation image G1 and outputs the ratio as an analysis result.

(c) Shape of Lesion Region Ln

When this item is selected as the analysis item, processing (S14) explained below is performed. A lesion-shape analyzing section 361A3 shown in FIG. 9 relates to the processing of S14.

The lesion-shape analyzing section 361A3 performs identification classification based on a shape of the lesioned part. More specifically, the lesion-shape analyzing section 361A3 creates a mask image indicating a lesion region and calculates a shape feature value based on the image. The shape feature value is classified into, using a classifier such as an SVM, one of a plurality of classes generated by machine learning. As the shape feature value, a publicly-known parameter such as circularity, moment, or fractal dimension is used.

For example, in the case of a large intestine polyp, there are an elevated type (I type) and a superficial type (II type). As the elevated type, there are sessile (Is) without a constriction in a rising part, sub-sessile (Isp) with a constriction in a rising part, and pedunculate (Ip) with a peduncle. In the superficial type, the large intestine polyp is classified into an elevated type (IIa), a flat type (IIb), and a depressed type (IIc).

For example, in the case of a stomach polyp, there are a submucosal tumor type (an elevated I type), a sessile type (an elevated II type), a sub-sessile type (an elevated III type), and a pedunculate type (an elevated IV type). For example, in the case of a stomach cancer, the stomach cancer is classified into a superficial type (a 0 type), a tumorous type (a 1 type), an ulcerative and localized type (a 2 type), an infiltrative ulcerative type (a 3 type), and a diffuse infiltrative type (a 4 type), and the like.

As explained above, the lesion-shape analyzing section 361A3 identifies a shape of the lesioned part and outputs the shape as an analysis result.

(d) Size of Lesion Region Ln

When this item is selected as the analysis item, processing (S15) explained below is performed. A lesion-size estimating section 361A4 shown in FIG. 9 relates to the processing of S15.

First, the lesion-size estimating section 361A4 estimates image pickup distances to respective pixels in an image. The lesion-size estimating section 361A4 may perform the estimation of the image pickup distances using the method explained above or the like. The lesion-distance estimating section 361A1 may perform the processing and acquires a result.

Subsequently, the lesion-size estimating section 361A4 provides a threshold smaller than an image pickup distance of a pixel near a lesion and a threshold larger than the image pickup distance and extracts, through processing by using the thresholds, a region of an image pickup distance zone where the lesion is present. The lesion-size estimating section 361A4 calculates circularity of the region and, when the circularity is larger than a predetermined value, detects the region as a lumen.

Finally, the lesion-size estimating section 361A4 compares the lumen and the lesioned part and estimates a size of the lesioned part.

More specifically, the lesion-size estimating section 361A4 estimates an actual size of the lesion by calculating a ratio occupied by length of the lesion with respect to a circumferential length of the detected lumen. Note that it is also possible to set circumferential lengths of lumens in respective organ parts (positions) beforehand based on anatomy and improve accuracy of size estimation. For example, in the case of a large intestine examination, estimation of a part (position) of a lesioned part of a large intestine may be performed based on an insertion amount of the insertion section to improve the accuracy of the size estimation of the actual size of the lesion based on the ratio occupied by the length of the lesion with respect to the circumferential length of the lumen set beforehand in the part (position) of the estimated lesioned part.

As explained above, the lesion-size estimating section 361A4 estimates the size of the lesioned part in comparison with the circular size of the lumen photographed in the endoscopic image and outputs the size of the lesioned part as an analysis result.

(e) Position of Lesion Region Ln in Observation Image G1

When this item is selected as the analysis item, processing (S16) explained below is performed. A lesion-position analyzing section 361A5 shown in FIG. 9 relates to the processing of S16.

First, the lesion-position analyzing section 361A5 detects the lesion region Ln from the observation image G1 and acquires position information by performing processing for applying, to the observation image G1, an image identifier that acquires, in advance, a function capable of identifying a polyp image with a learning method such as deep learning. Note that the detection of the lesion region Ln is not limited to the learning method explained above and other methods may be used. For example, polyp candidate detection processing disclosed in Japanese Patent Application Laid-Open Publication No. 2007-244518 may be used. The position information of the lesion region Ln may be acquired from the lesion detecting section 34 or the lesion-occupied-area calculating section 361A2.

Subsequently, the lesion-position analyzing section 361A5 analyzes a position of the lesion region Ln in the observation image G1. An example of a specific method is explained below. First, the observation image G1 is equally divided into three in a vertical direction, and equally divided into three in the horizontal direction, thus divided into nine blocks. For example, when the observation image G1 includes 1920×1080 pixels, when the upper left of the image is assumed to be an origin (0, 0), the lesion-position analyzing section 361A5 divides the observation image G1 into a region (1A) of (0, 0) to (640, 360), a region (1B) of (641, 0) to (1280, 360), a region (1C) of (1281, 0) to (1920, 360), a region (2A) of (0, 361) to (640, 720), a region (2B) of (641, 361) to (1280, 720), a region (2C) of (1281, 361) to (1920, 720), a region (3A) of (0, 721) to (640, 1080), a region (3B) of (641, 721) to (1280, 1080), and a region (3C) of (1281, 721) to (1920, 1080).

The lesion-position analyzing section 361A5 specifies, among the nine blocks 1A to 3C, a block where the lesion region Ln is present and outputs the block as a position of the lesion region Ln. Note that when the legion region Ln is present across a plurality of blocks, a block where an area of presence of the lesion region Ln is the largest is set as the block where the lesion region Ln is present. Note that a method of specifying the block where the lesion region Ln is present is not limited to the method explained above. Other methods may be used such as a method of setting, as the block where the lesion region Ln is present, a block where a pixel located in a center of the lesion region Ln is present. The number of blocks generated by dividing the observation image G1 is not limited to nine and may be, for example, 2×2=4 blocks or 4×4=16 blocks.

The position of the lesion region Ln may not be the block position explained above and may be calculated as a distance from a center pixel position of the observation image G1.

As explained above, the lesion-position analyzing section 361A5 specifies the position of the lesion region Ln in the observation image G1 and outputs the position as an analysis result.

(f) Color and Luminance of Lesion Region Ln

When this item is selected as the analysis item, processing (S17) explained below is performed. A lesion-color/luminance analyzing section 361A6 shown in FIG. 9 relates to the processing of S17.

When the observation image G1 is an image formed by three components of red (R), green (G), and blue (B), the lesion-color/luminance analyzing section 361A6 extracts pixel values (R pixel values, G pixel values, and B pixel values) of respective pixels included in the lesion region Ln. The lesion-color/luminance analyzing section 361A6 calculates an average of each of the R pixel values, the G pixel values, and the B pixel values and sets the average as a color pixel value of the lesion region Ln. Note that other statistical values such as a mode may be used for calculation of a pixel value of the lesion region Ln rather than the average.

The lesion-color/luminance analyzing section 361A6 extracts luminance values of the respective pixels included in the lesion region Ln, calculates an average value of the luminance values, and sets the average value as a luminance value of the lesion region Ln. Note that other statistical values such as a mode may be used for calculation of a luminance value of the lesion region Ln rather than the average.

As explained above, the lesion-color/luminance analyzing section 361A6 calculates the color pixel value and the luminance value of the lesion region Ln in the observation image G1 and outputs the color pixel value and the luminance value as an analysis result.

(g) Organ Part where Lesion Region Ln is Located

When this item is selected as the analysis item, processing (S18) explained below is performed. An organ-part analyzing section 361A7 shown in FIG. 9 relates to the processing of S18.

The organ-part analyzing section 361A7 performs estimation of an observation part. For example, when an organ to be observed is a large intestine, the organ-part analyzing section 361A7 recognizes a rectum, a sigmoid colon, a descending colon, a left flexure of colon (a splenic flexure), a transverse colon, a right flexure of colon (a hepatic flexure), an ascending colon, and a caecum. When the organ to be observed is a stomach, the organ-part analyzing section 361A7 recognizes a cardiac orifice, a stomach fundus, a gastric corpus, a gastric angle, a vestibule, a pyloric region, a pylorus, and a duodenum. In the case of a small intestine, the organ-part analyzing section 361A7 recognizes a jejunum and an ileum. In the case of an esophagus, the organ-part analyzing section 361A7 recognizes a cervical esophagus, a thoracic esophagus, and an abdominal esophagus. More specifically, the organ-part analyzing section 361A7 can perform part (position) estimation using an SVM or the like by collecting image data in which the large intestine, the stomach, the small intestine, and the esophagus are photographed and performing machine learning using the image data.

As explained above, the organ-part analyzing section 361A7 estimates the observation part and outputs the observation part as an analysis result.

When the processing of the selected one or more items among the processing of S12 to the processing of S18 ends, the lesion-state analyzing section 36b determines visibility based on analysis results of these kinds of processing (S19). First, the lesion-state analyzing section 36b determines visibility for each of the analysis items.

(a) Distance Between Endoscope 21 and Lesion Region Ln.

When the distance between the endoscope 21 and the lesion region Ln outputted from the lesion-distance estimating section 361A1 as the analysis result is larger than a predetermined distance set in advance, the lesion-state analyzing section 36b determines that the visibility is low. On the other hand, when the distance between the endoscope 21 and the lesion region Ln is equal to or smaller than the predetermined distance, the lesion-state analyzing section 36b determines that the visibility is high.

(b) Ratio of Occupied Area of Lesion Region Ln in Observation Image G1

When the occupancy ratio of the lesion region Ln outputted from the lesion-occupied-area calculating section 361A2 as an analysis result is equal to or lower than a predetermined ratio (for example, 5 percent) set in advance, the lesion-state analyzing section 36b determines that the visibility is low. On the other hand, when the occupancy ratio of the lesion region Ln is higher than the predetermined ratio, the lesion-state analyzing section 36b determines that the visibility is high.

(c) Shape of Lesion Region Ln

When the shape of the lesion region Ln outputted from the lesion-shape analyzing section 361A3 as the analysis result corresponds to a shape with high visibility set in advance, the lesion-state analyzing section 36b determines that the visibility is high. For example, shapes described below are set as the shape with high visibility.

When the lesioned part is a large intestine: a superficial flat type (IIb) and a superficial depressed type (IIc).

When the lesioned part is a stomach: a submucosal tumor type (an elevated I type).

When the shape of the lesion region Ln corresponds to a shape with low visibility set in advance, the lesion-state analyzing section 36b determines that the visibility is low. For example, shapes described below are set as the shape with low visibility.

When the lesioned part is a large intestine: sessile (Is), sub-sessile (Isp), pedunculate (Ip), and a superficial elevated type (IIa).

When the lesioned part is a stomach: a sessile type (an elevated II type), a sub-sessile type (an elevated III type), a pedunculate type (an elevated IV type), a tumorous type (a 1 type), an ulcerative and localized type (a 2 type), an infiltrative ulcerative type (a 3 type), and a diffuse infiltrative type (a 4 type).

(d) Size of Lesion Region Ln

When the size of the lesion region Ln outputted from the lesion-size estimating section 361A4 as the analysis result is equal to or smaller than a predetermined size (for example, 5 mm) set in advance, the lesion-state analyzing section 36b determines that the visibility is low. On the other hand, when the size of the lesion region Ln is larger than the predetermined size, the lesion-state analyzing section 36b determines that the visibility is high.

(e) Position of Lesion Region Ln in Observation Image G1

The lesion-state analyzing section 36b determines visibility according to the position of the lesion region Ln outputted from the lesion-position analyzing section 361A5 as the analysis result. In other words, when the position of the lesion region Ln is apart from the image center, the lesion-state analyzing section 36b determines that the visibility is low. On the other hand, when the position of the lesion region Ln is close to the image center, the lesion-state analyzing section 36b determines that the visibility is high.

For example, when the block position where the lesion region Ln is present is outputted as the analysis result, the lesion-state analyzing section 36b sets, as a determination result, visibility registered for each of blocks in advance. More specifically, it is assumed that, for example, the observation image G1 is divided into 3×3=9 blocks, four blocks (blocks 1A, 3A, 1C, and 3C) located at four corners of an image are registered as having low visibility, and the other five blocks (blocks 2A, 1B, 2B, 3B, and 2C) are registered as having high visibility. In this case, if the block position where the lesion region Ln is present is the block 1A, 3A, 1C, or 3C, the lesion-state analyzing section 36b determines that the visibility is low. If the block position where the lesion region Ln is present is the block 2A, 1B, 2B, 3B, or 2C, the lesion-state analyzing section 36b determines that the visibility is high.

When the distance from the center pixel position of the observation image G1 is outputted as the analysis result, the lesion-state analyzing section 36b determines that the visibility is low when the distance is larger than a predetermined distance set in advance. On the other hand, the lesion-state analyzing section 36b determines that the visibility is high when the distance is equal to or smaller than the predetermined distance.

(f) Color and Luminance of Lesion Region Ln

When the color and the luminance of the lesion region Ln outputted from the lesion-color/luminance analyzing section 361A6 as the analysis result are close to a color and luminance of a normal mucous membrane, the lesion-state analyzing section 36b determines that the visibility is low. On the other hand, when the color and the luminance of the lesion region Ln are different from the color and the luminance of the normal mucous membrane, the lesion-state analyzing section 36b determines that the visibility is high. As the color (a color pixel value) and the luminance (a luminance value) of the normal mucous membrane serving as a determination reference, a color and luminance registered in advance may be used or values of a normal mucous membrane portion in the observation image G1 in which the lesion region Ln is present may be used.

(g) Organ Part where Lesion Region Ln is Located

When the organ part where the lesion region Ln is located outputted from the organ-part analyzing section 361A7 as the analysis result corresponds to a part with high visibility set in advance, the lesion-state analyzing section 36b determines that the visibility is high. For example, organ parts described below are set as parts with high visibility.

When the lesioned part is a large intestine: a descending colon, a transverse colon, and a cecum.

When the lesioned part is a stomach: a cardiac orifice, a stomach fundus, a gastric corpus, a gastric angle, a vestibule, a pyloric region, a pylorus, and a duodenum.

When the lesioned part is a small intestine: a jejunum and an ileum.

When the lesioned part is an esophagus: a cervical esophagus, a thoracic esophagus, and an abdominal esophagus.

When the organ part where the lesion region Ln is located corresponds to a part with low visibility set in advance, the lesion-state analyzing section 36b determines that the visibility is low. For example, organ parts described below are set as parts with low visibility.

When the lesioned part is a large intestine: a rectum, a sigmoid colon, a left flexure of colon (a splenic flexure), a right flexure of colon (a hepatic flexure), and an ascending colon.

In other words, when the organ part where the lesion region Ln is located is a part where lesions frequently occur or a part where an examination image is hard to see and a lesion tends to be overlooked, the lesion-state analyzing section 36b determines that the organ part is the part with low visibility.

When only one item is selected as the analysis item of visibility in S11, the lesion-state analyzing section 36b outputs, as the visibility of the lesion region Ln, a visibility determination result concerning the item and ends a series of lesion analysis processing. When two or more items are selected as the analysis item of visibility in S11, the lesion-state analyzing section 36b refers to visibility determination results of the selected items and determines the visibility of the lesion region Ln.

Examples of a method of determining visibility when a plurality of items are selected include a majority method. In other words, when the number of items determined as having high visibility is larger than the number of items determined as having low visibility in visibility determination results of selected items, the lesion-state analyzing section 36b determines that the visibility of the lesion region Ln is high. On the other hand, when the number of items determined as having high visibility is equal to or smaller than the number of items determined as having low visibility, the lesion-state analyzing section 36b determines that the visibility of the lesion region Ln is low.

Examples of another determination method include a point method. In other words, according to the visibility, a point is given to each of the respective items (a) to (g) explained above. For example, in the respective items, +1 point is given when it is determined that the visibility is low and −1 point is given when it is determined that the visibility is high. Note that, concerning items particularly contributing to the visibility (for example, the item (c) and the item (e)), points weighted compared with the other items may be set to be given, for example, +3 points are given when it is determined that the visibility is low and −3 points are given when it is determined that the visibility is high.

When the visibility determination results of the selected items are converted into points and a sum of the points is calculated and the sum of the points is larger than a threshold (for example, 1 point) set in advance, the lesion-state analyzing section 36b determines that the visibility of the lesion region Ln is low and outputs a determination result. On the other hand, when the sum of the points is equal to or smaller than the threshold set in advance, the lesion-state analyzing section 36b determines that the visibility of the legion region Ln is high and outputs a determination result.

The determination result is outputted to the display-extension-time setting section 36c. The display-extension-time setting section 36c selects an appropriate display extension time based on the visibility determination result of the lesion-state analyzing section 36b. In other words, the display-extension-time setting section 36c sets a display extension time longer as the visibility is lower. The display-extension-time setting section 36c may calculate the display extension time based on the visibility determination result. For example, concerning each of the respective items (a) to (g) explained above, an increase or decrease value of display extension time (the number of frames) is set in advance according to a detection result. For example, concerning the item (d) a size of the lesion region Ln, the increase or decrease value is set as −2 frames in the case of a large size, set as ±0 frame in the case of a normal size, and set as +2 frames in the case of a small size. For example, concerning the item (a) a distance between the endoscope 21 and the lesion region Ln, the increase or decrease value is set as +2 frames when the distance is longer than a predetermined distance range, set as ±0 frame when the distance is within a predetermined range, and set as −2 frames when the distance is shorter than the predetermined distance range. In this way, the increase or decrease values are set for all items. It is also possible to calculate a sum of increase or decrease values of the display extension time (the number of frames) based on the visibility determination results of the selected items and set the display extension time.

Note that when the point method is used, the visibility determination in the respective items (a) to (g) may also be performed by the point method. For example, concerning the item (d), −1 point is given when the position of the lesion region Ln is present within a range of the center pixel position of the observation image G1 to a first threshold, 0 point is given when the position of the lesion region Ln is present within a range of the first threshold to a second threshold, and +1 point is given when the position of the lesion region Ln is present within a range of the second threshold to a third threshold (the first threshold<the second threshold<the third threshold). A method of outputting a given point as a determination result of the visibility and, in S19, calculating a sum of points outputted as determination results of the respective items may be used.

As explained above, according to the embodiment explained above, by adjusting, based on the visibility of the lesion region Ln analyzed by the lesion-state analyzing section 36b, the time period (the display extension time) in which the marker image G2 is continuously displayed after the detection of the lesion region Ln is interrupted, it is possible to reduce overlooking of the lesioned part that could occur in the endoscopic observation and improve the visibility.

Modification of the Second Embodiment

In the second embodiment explained above, the visibility is determined in a lesion unit. However, in the modification, the visibility is determined in an image unit.

Figure 11:
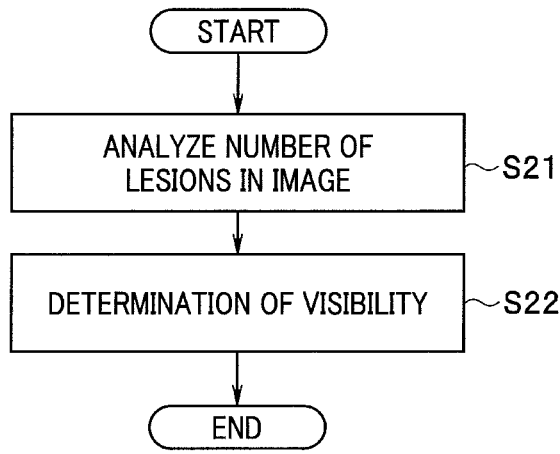
FIG. 11 is a flowchart showing an example of a flow of lesion analysis processing according to a modification of the second embodiment.

FIG. 11 is a flowchart showing an example of a flow of lesion analysis processing according to the modification. The visibility analyzing section 361, in particular, an image-unit-information analyzing section 361B in the lesion-state analyzing section 36b shown in FIG. 9 relates to the processing shown in FIG. 11.

The lesion-state analyzing section 36b analyzes the visibility of the lesion region Ln in the observation image G1. When the visibility is analyzed in an image unit, a number-of-lesions analyzing section 361B1 extracts the number of lesion regions Ln present in the observation image G1 (S21).

Subsequently, the lesion-state analyzing section 36b determines visibility of the observation image G1 based on the number of lesion regions Ln extracted by the number-of-lesions analyzing section 361B1 (S22). In other words, when the number of lesion regions Ln is larger than a threshold (for example, three) set in advance, the lesion-state analyzing section 36b determines that the visibility is low. On the other hand, when the number of lesion regions Ln is equal to or smaller than the threshold set in advance, the lesion-state analyzing section 36b determines that the visibility is high.

A determination result is outputted to the display-extension-time setting section 36c. The display-extension-time setting section 36c selects an appropriate display extension time based on the visibility determination result of the lesion-state analyzing section 36b.

Note that the determination of the visibility may be performed using both of the analysis result in an image unit and the analysis result in a lesion unit. In other words, after a series of procedures of S11 to S18 shown in FIG. 10 is performed to analyze the visibility in a lesion unit, a procedure of S21 shown in FIG. 11 is subsequently performed. The determination of the visibility may be comprehensively performed using an analysis result in a lesion unit and an analysis result in an image unit acquired by these procedures.

As explained above, according to the modification, it is possible to obtain the same effects as the effects of the respective embodiments explained above.

Third Embodiment

In the second embodiment explained above, according to the visibility of the lesion region Ln, the time period (the display extension time) in which the marker image G2 is continuously displayed after the detection of the lesion region Ln is interrupted. However, in the present embodiment, importance of the lesion region Ln is analyzed and a display extension time is determined based on a result of the analysis.

An image processing apparatus in the present embodiment has the same configuration as the configuration of the image processing apparatus 32 in the first embodiment. The same components are denoted by the same reference numerals and signs and explanation of the components is omitted.

Figure 12:
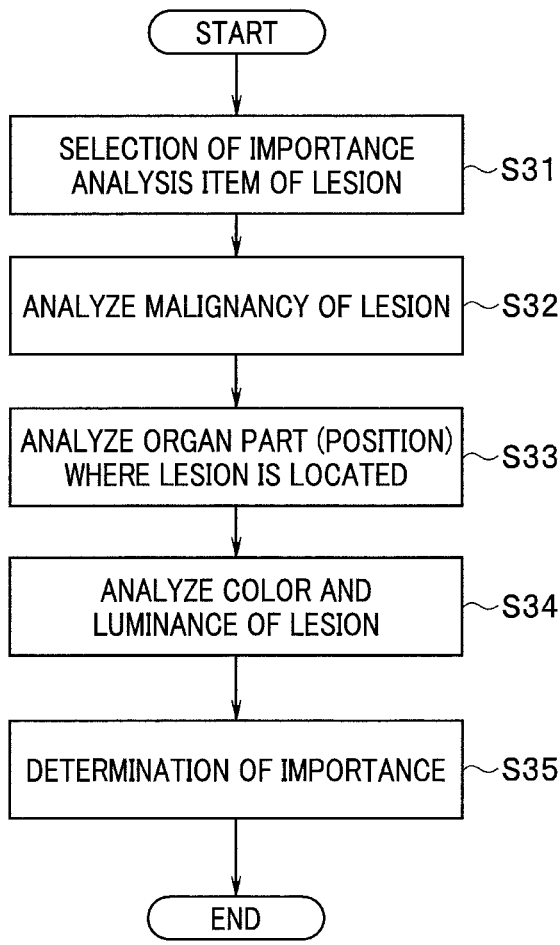
FIG. 12 is a flowchart showing an example of a flow of lesion analysis processing according to a third embodiment.

FIG. 12 is a flowchart showing an example of a flow of lesion analysis processing according to the third embodiment. An importance analyzing section 362, in particular, a lesion-type analyzing section 362A in the lesion-state analyzing section 36b shown in FIG. 9 relates to the processing shown in FIG. 12.

The lesion-state analyzing section 36b analyzes importance of the lesion region Ln. First, the lesion-state analyzing section 36b selects an item for which an analysis of importance is performed (S31). Examples of analysis items of importance include items such as (h) malignancy of the lesion region Ln, (i) an organ part where the lesion region Ln is located, and (j) a color and luminance of the lesion region Ln. The lesion-state analyzing section 36b performs an analysis concerning items selected out of these items. Note that the analysis of importance may be performed by selecting only one item or may be performed by selecting a plurality of items.

(h) Malignancy of Lesion Region Ln

When this item is selected as the analysis item, processing (S21) explained below is performed. A malignancy analyzing section 362A1 shown in FIG. 9 relates to the processing of S21.

The malignancy analyzing section 362A1 classifies malignancy of the lesion region Ln. The classification of the malignancy is selected by an observation method. For example, when a narrowband observation is performed, the malignancy of the lesion region Ln is classified using an existing malignancy classification such as a NICE (NBI International Colorectal Endoscopic) classification or a JNET (The Japan NBI Expert Team) classification.

The NICE classification is a simple category classification of three Types 1 to 3. Classification is performed from three viewpoints of (1) color tone (color), (2) microvasculature construction (vessels), and (3) surface structure (surface pattern). Type 1 is an indicator of non-tumor, Type 2 is an indicator of adenoma to intramucosal carcinoma, and Type 3 is an indicator of SM massively invasive cancer.

In the case of a dye magnifying observation, the malignancy of the lesion region Ln is classified using a PIT pattern classification or the like.

As explained above, the malignancy analyzing section 362A1 classifies the malignancy of the lesion region Ln and outputs the malignancy of the lesion region Ln as an analysis result.

(i) Organ Part where Lesion Region Ln is Located

When this item is selected as the analysis item, processing (S33) explained below is performed. An organ-part analyzing section 362A2 shown in FIG. 9 relates to the processing of S33.

The organ-part analyzing section 362A2 performs estimation of an observation part. For example, when an organ to be observed is a large intestine, the organ-part analyzing section 362A2 recognizes a rectum, a sigmoid colon, a descending colon, a left flexure of colon (a splenic flexure), a transverse colon, a right flexure of colon (a hepatic flexure), an ascending colon, and a caecum. When the organ to be observed is a stomach, the organ-part analyzing section 362A2 recognizes a cardiac orifice, a stomach fundus, a gastric corpus, a gastric angle, a vestibule, a pyloric region, a pylorus, and a duodenum. In the case of a small intestine, the organ-part analyzing section 362A2 recognizes a jejunum and an ileum. In the case of an esophagus, the organ-part analyzing section 362A2 recognizes a cervical esophagus, a thoracic esophagus, and an abdominal esophagus. More specifically, the organ-part analyzing section 362A2 can perform part (position) estimation using an SVM or the like by collecting image data in which the large intestine, the stomach, the small intestine, and the esophagus are photographed and performing machine learning using the image data.

As explained above, the organ-part analyzing section 362A2 estimates an observation part and outputs the observation part as an analysis result. Note that processing content of the organ-part analyzing section 362A2 is the same as the processing content of the organ-part analyzing section 361A7. Therefore, the result of the organ-part analyzing section 361A7 may be used.

(j) Color and Luminance of Lesion Region Ln

When this item is selected as the analysis item, processing (S34) explained below is performed. A lesion-color/luminance analyzing section 362A3 shown in FIG. 9 relates to the processing of S34.

When the observation image G1 is an image formed by three components of red (R), green (G), and blue (B), the lesion-color/luminance analyzing section 362A3 extracts pixel values (R pixel values, G pixel values, and B pixel values) of respective pixels included in the lesion region Ln. The lesion-color/luminance analyzing section 362A3 calculates an average of each of the R pixel values, the G pixel values, and the B pixel values and sets the average as a color pixel value of the lesion region Ln. Note that other statistical values such as a mode may be used for calculation of a pixel value of the lesion region Ln rather than the average.

The lesion-color/luminance analyzing section 362A3 extracts luminance values of the respective pixels included in the lesion region Ln, calculates an average value of the luminance values, and sets the average value as a luminance value of the lesion region Ln. Note that other statistical values such as a mode may be used for calculation of a luminance value of the lesion region Ln rather than the average.

As explained above, the lesion-color/luminance analyzing section 362A3 calculates the color pixel value and the luminance value of the lesion region Ln in the observation image G1 and outputs the color pixel value and the luminance value as an analysis result. Note that processing content of the lesion-color/luminance analyzing section 362A3 is the same as the processing content of the lesion-color/luminance analyzing section 361A6. Therefore, the processing result of the lesion-color/luminance analyzing section 361A6 may be used.

When processing of selected one or more items among the processing of S32 to the processing of S34 ends, the lesion-state analyzing section 36b determines importance based on analysis results of these items (S35). First, the lesion-state analyzing section 36b determines importance for each of the analysis items.

(h) Malignancy of Lesion Region Ln

When the malignancy of the lesion region Ln outputted from the malignancy analyzing section 362A1 as the analysis result corresponds to a category set in advance, the lesion-state analyzing section 36b determines that the importance is high.

(i) Organ Part where Lesion Region Ln is Located

When the organ part where the lesion region Ln is located outputted from the organ-part analyzing section 362A2 as the analysis result corresponds to a part with high importance set in advance, the lesion-state analyzing section 36b determines that the importance is high. For example, organ parts described below are set as parts with high importance.

When the lesioned part is a large intestine: a sigmoid colon.

When the organ part where the lesion region Ln is located is other than the part described above, the lesion-state analyzing section 36b determines that the importance is low. In other words, in the case of a part where a risk of worsening of a symptom is high if unattended, the lesion-state analyzing section 36b determines the part as a part with high importance. Note that the organ part where the lesion region Ln is located is also described as the determination item of the visibility. However, a level of the visibility and a level of the importance are respectively determined by independent evaluation indicators.

(j) Color and Luminance of Lesion Region Ln

When the color and luminance of the lesion region Ln outputted from the lesion-color/luminance analyzing section 362A3 as the analysis result are close to a color and luminance of a lesioned part with high importance registered in advance, the lesion-state analyzing section 36b determines that the importance is high. Note that the color and luminance of the lesion region Ln are also described as the determination item of the visibility. However, a level of the visibility and a level of the importance are respectively determined by independent evaluation indicators.

When only one item is selected as the analysis item of importance in S31, the lesion-state analyzing section 36b outputs an importance determination result concerning the item as the importance of the lesion region Ln and ends a series of lesion analysis processing. When two or more items are selected as the analysis item of importance in S31, the lesion-state analyzing section 36b refers to importance determination results of the selected items and determines the importance of the lesion region Ln.

As a method of determining importance when a plurality of items are selected, the majority method and the point method can be used as in the case of the determination method for visibility.

The determination result is outputted to the display-extension-time setting section 36c. The display-extension-time setting section 36c selects an appropriate display extension time based on the importance determination result of the lesion-state analyzing section 36b. In other words, the display-extension-time setting section 36c sets the display extension time longer as the importance is higher.

As explained above, according to the embodiment explained above, by adjusting, based on the importance of the lesion region Ln analyzed by the lesion-state analyzing section 36b, the time period (the display extension time) in which the marker image G2 is continuously displayed after the detection of the lesion region Ln is interrupted, it is possible to reduce overlooking of the lesioned part that could occur in the endoscopic observation and improve the visibility.

Modification of the Third Embodiment

In the third embodiment explained above, the importance is determined based on the type of the lesion. However, in the modification, the importance is determined according to a shape and a size of the lesion.

Figure 13:
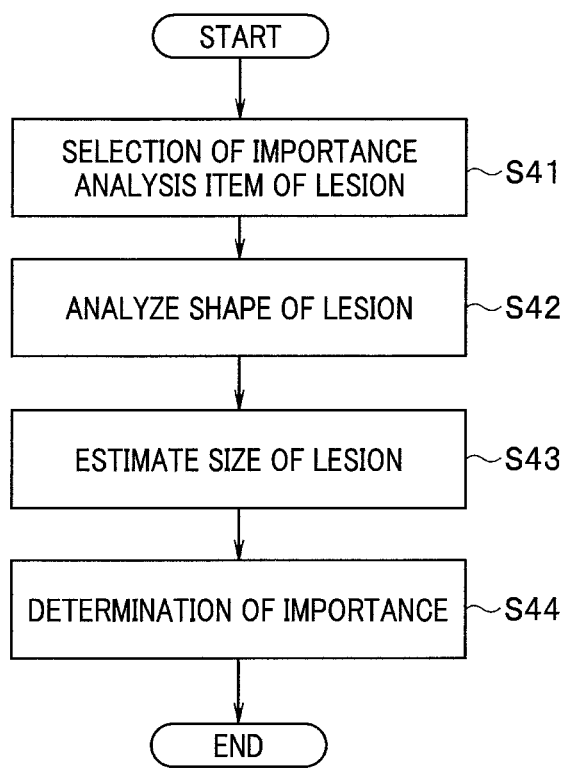
FIG. 13 is a flowchart showing an example of a flow of lesion analysis processing according to a modification of the third embodiment.

FIG. 13 is a flowchart showing an example of a flow of lesion analysis processing according to the modification. The importance analyzing section 362, in particular, a lesion-shape/size analyzing section 362B in the lesion-state analyzing section 36b shown in FIG. 9 relates to the processing shown in FIG. 13.

The lesion-state analyzing section 36b analyzes the importance of the lesion region Ln. First, the lesion-state analyzing section 36b selects an item for which an analysis of importance is performed (S41). Examples of analysis items of importance concerning a shape and a size of a lesion include items such as (k) a shape of the lesion region Ln and (l) a size of the lesion region Ln. The lesion-state analyzing section 36b performs an analysis concerning items selected out of these items. Note that the analysis of the importance may be performed by selecting only one item or may be performed by selecting a plurality of items.

(k) Shape of Lesion Region Ln

When this item is selected as the analysis item, processing (S42) explained below is performed. A lesion-shape analyzing section 362B1 shown in FIG. 9 relates to the processing of S42.

The lesion-shape analyzing section 362B1 performs identification classification based on a shape of a lesioned part. More specifically, the lesion-shape analyzing section 362B1 creates a mask image indicating a lesion region and calculates a shape feature value based on the image. The shape feature value is classified into, using a classifier such as an SVM, one of a plurality of classes generated by machine learning. As the shape feature value, a publicly-known parameter such as circularity, moment, or fractal dimension is used.

For example, in the case of a large intestine polyp, there are an elevated type (I type) and a superficial type (II type). As the elevated type, there are sessile (Is) without a constriction in a rising part, sub-sessile (Isp) with a constriction in a rising part, and pedunculate (Ip) with a peduncle. In the superficial type, the large intestine polyp is classified into an elevated type (IIa), a flat type (IIb), and a depressed type (IIc).

For example, in the case of a stomach polyp, there are a submucosal tumor type (an elevated I type), a sessile type (an elevated II type), a sub-sessile type (an elevated III type), and a pedunculate type (an elevated IV type). For example, in the case of a stomach cancer, the stomach cancer is classified into a superficial type (a 0 type), a tumorous type (a 1 type), an ulcerative and localized type (a 2 type), an infiltrative ulcerative type (a 3 type), and a diffuse infiltrative type (a 4 type), and the like.

As explained above, the lesion-shape analyzing section 362B1 identifies a shape of the lesioned part and outputs the shape as an analysis result. Note that processing content of the lesion-shape analyzing section 362B1 is the same as the processing content of the lesion-shape analyzing section 361A3. Therefore, the result of the lesion-shape analyzing section 361A3 may be used.

(l) Size of Lesion Region Ln

When this item is selected as the analysis item, processing (S43) explained below is performed. A lesion-size estimating section 362B2 shown in FIG. 9 relates to the processing of S43.

First, the lesion-size estimating section 362B2 estimates image pickup distances to respective pixels in an image. The lesion-size estimating section 362B2 may perform the estimation of the image pickup distances using the method explained above or the like. The lesion-distance estimating section 361A1 may perform the processing and acquire the result.

Subsequently, the lesion-size estimating section 362B2 provides a threshold smaller than an image pickup distance of a pixel near a lesion and a threshold larger than the image pickup distance and extracts, through processing by using the thresholds, a region of an image pickup distance zone where the lesion is present. The lesion-size estimating section 362B2 calculates circularity of the region and, when the circularity is larger than a predetermined value, detects the region as a lumen.

Finally, the lesion-size estimating section 362B2 compares the lumen and the lesioned part and estimates a size of the lesioned part.

More specifically, the lesion-size estimating section 362B2 estimates an actual size of the lesion by calculating a ratio occupied by length of the lesion with respect to a circumferential length of the detected lumen. Note that it is also possible to set circumferential lengths of lumens in respective organ parts (positions) beforehand based on anatomy and improve accuracy of size estimation. For example, in the case of a large intestine examination, estimation of a part (position) of a lesioned part of a large intestine may be performed based on an insertion amount of the insertion section to improve the accuracy of the size estimation of the actual size of the lesion based on the ratio occupied by the length of the lesion with respect to the circumferential length of the lumen set beforehand in the part (position) of the estimated lesioned part.

As explained above, the lesion-size estimating section 362B2 estimates the size of the lesioned part in comparison with the circular size of the lumen photographed in the endoscopic image and outputs the size of the lesioned part as an analysis result. Note that processing content of the lesion-size estimating section 362B2 is the same as the processing content of the lesion-size estimating section 361A4. Therefore, the result of the lesion-size estimating section 361A4 may be used.

When processing of selected one or more items of the processing of S42 and the processing of S43 ends, the lesion-state analyzing section 36b determines importance based on analysis results of the items (S44). First, the lesion-state analyzing section 36b determines importance for each of analysis items.

(k) Shape of Lesion Region Ln

When the shape of the lesion region Ln outputted from the lesion-shape analyzing section 362B1 as the analysis result corresponds to a shape with high importance set in advance, the lesion-state analyzing section 36b determines that the importance is high. For example, shapes described below are set as the shape with high importance.

When the lesioned part is a large intestine: a superficial flat type (IIb) and a superficial depressed type (IIc).

When the lesioned part is a stomach: a tumorous type (a 1 type), an ulcerative and localized type (a 2 type), an infiltrative ulcerative type (a 3 type), and a diffuse infiltrative type (a 4 type).

When the shape of the lesion region Ln is other than the shapes described above, the lesion-state analyzing section 36b determines that the importance is low. In other words, in the case of the shape of the lesion region Ln with a high risk of worsening of a symptom if unattended, the lesion-state analyzing section 36b determines the lesion region Ln as a part with high importance. Note that the shape of the lesion region Ln is also described as the determination item of the visibility. However, a level of the visibility and a level of the importance are respectively determined by independent evaluation indicators.

(l) Size of Lesion Region Ln

When the size of the lesion region Ln outputted from the lesion-size estimating section 362B2 as the analysis result is equal to or smaller than a predetermined size (for example, 5 mm) set in advance, the lesion-state analyzing section 36b determines that the importance is low. On the other hand, when the size of the lesion region Ln is larger than the predetermined size, the lesion-state analyzing section 36b determines that the importance is high. Note that the size of the lesion region Ln is also described as the determination item of the visibility. However, a level of the visibility and a level of the importance are respectively determined by independent evaluation indicators.

As a method of determining importance when a plurality of items are selected, the majority method and the point method can be used as in the case of the determination method for visibility.

The determination result is outputted to the display-extension-time setting section 36c. The display-extension-time setting section 36c selects an appropriate display extension time based on the importance determination result of the lesion-state analyzing section 36b. In other words, the display-extension-time setting section 36c sets the display extension time longer as the importance is higher.

Note that the determination of the importance may be performed using both of the analysis result based on the lesion type and the analysis result based on the lesion shape and size. In other words, after a series of procedures of S31 to S34 shown in FIG. 12 is performed to perform the analysis of the importance based on the lesion type, the procedures of S41 to S43 shown in FIG. 13 are subsequently performed. The determination of the importance may be comprehensively performed using the analysis result based on the lesion type and the analysis result based on the lesion shape and size acquired by these procedures.

A state of a lesion may be determined using both of the analysis result of the visibility and the analysis result of the importance.

As explained above, according to the embodiments and the modifications explained above, it is possible to provide an image processing apparatus for endoscope that can reduce overlooking of a lesioned part that could occur in an endoscopic observation and improve visibility by adjusting, according to a state of the lesion region Ln, a time period (a display extension time) in which the marker image G2 is continuously displayed after the detection of the lesion region Ln is interrupted.

The present invention is not limited to the embodiments explained above. It goes without saying that various changes and applications are possible within a range not departing from the gist of the invention.

What is claimed is:

1. An image processing apparatus comprising:
a processor configured to:
    receive an observation image obtained by picking up an image of an object with an endoscope;
    detect one or more lesioned parts, which each is an observation target of the endoscope, from the observation image;
    perform highlighting processing on each of the one or more lesioned parts;
    analyze visibility of each of the one or more lesioned parts;
    analyze an importance of the each of the one or more lesioned parts;
    set a display extension time of the highlighting processing of each of the one or more lesioned parts according to the analyzed visibility and the analyzed importance; and
    output the observation image to which each of the one or more lesioned parts on which the highlighting processing has been performed is added.

2. The image processing apparatus according to claim 1, wherein the processor is configured to:
    estimate a distance of the each of the one or more lesioned parts from the endoscope; and
    analyze the visibility of the each of the one or more lesioned parts based on the distance of the each of the one or more lesioned parts from the endo scope estimated.

3. The image processing apparatus according to claim 1, wherein the processor is configured to:
    calculate an occupied area of the each of the one or more lesioned parts in the observation image; and
    analyze the visibility of the each of the one or more lesioned parts based on the occupied area of the each of the one or more lesioned parts in the observation image calculated.

4. The image processing apparatus according to claim 1, wherein the processor is configured to:
    analyze a shape of the each of the one or more lesioned parts; and
    analyze the visibility of the each of the one or more lesioned parts based on the shape of the each of the one or more lesioned parts analyzed.

5. The image processing apparatus according to claim 4, wherein, when an observation target organ part of the endoscope is a large intestine, the processor is configured to:
    analyze which shape of sessile, sub-sessile, pedunculate, a superficial elevated type, a superficial flat type, and a superficial depressed type the shape of the each of the one or more lesioned parts is; and
    analyze the visibility of the each of the one or more lesioned parts based on the shape of sessile, sub-sessile, pedunculate, the superficial elevated type, the superficial flat type, and the superficial depressed type the shape of the each of the one or more lesioned parts is analyzed to be, and
wherein, when the observation target organ part is a stomach, the processor is configured to:
    analyze which shape of a submucosal tumor type, a sessile type, a sub-sessile type, a pedunculate type, a superficial type, a tumorous type, an ulcerative and localized type, an infiltrative ulcerative type, and a diffuse infiltrative type the shape of the each of the one or more lesioned parts is; and
    analyze the visibility of the each of the one or more lesioned parts based on the shape of the submucosal tumor type, the sessile type, the sub-sessile type, the pedunculate type, the superficial type, the tumorous type, the ulcerative and localized type, the infiltrative ulcerative type, and the diffuse infiltrative type the shape of the each of the one or more lesioned parts is analyzed to be.

6. The image processing apparatus according to claim 1, wherein the processor is configured to:
   estimate a size of the each of the one or more lesioned parts; and
   analyze the visibility of the each of the one or more lesioned parts based on the size of the each of the one or more lesioned parts estimated.

7. The image processing apparatus according to claim 1, wherein the processor is configured to:
   analyze a position of the each of the one or more lesioned parts; and
   analyze the visibility of the each of the one or more lesioned parts based on the position of the each of the one or more lesioned parts analyzed.

8. The image processing apparatus according to claim 1, wherein the processor is configured to:
   analyze at least one of a color or luminance of the each of the one or more lesioned parts; and
   analyze the visibility of the each of the one or more lesioned parts based on the at least one or of the color or luminance of the each of the one or more lesioned parts analyzed.

9. The image processing apparatus according to claim 1, wherein the processor is configured to:
   analyze an organ part
   where the each of the one or more lesioned parts is located; and
   analyze the visibility of the each of the detected one or more lesioned parts based on the organ part analyzed.

10. The image processing apparatus according to claim 9, wherein, when the organ part is a large intestine, the processor is configured to:
    estimate which of a rectum, a sigmoid colon, a descending colon, a left flexure of colon, a transverse colon, a right flexure of colon, an ascending colon, and a caecum the each of the one or more lesioned parts is located; and
    analyze the visibility of the each of the one or more lesioned parts based on the rectum, the sigmoid colon, the descending colon, the left flexure of colon, the transverse colon, the right flexure of colon, the ascending colon and the caecum that the each of the one or more lesioned parts is estimated to be located,
    wherein, when the organ part is a stomach, the processor is configured to:
    estimate which of a cardiac orifice, a stomach fundus, a gastric corpus, a gastric angle, a vestibule, a pyloric region, a pylorus, and a duodenum the each of the one or more lesioned parts is located; and
    analyze the visibility of the each of the one or more lesioned parts based on the cardiac orifice, the stomach fundus, the gastric corpus, the gastric angle, the vestibule, the pyloric region, the pylorus and the duodenum that the each of the one or more lesioned parts is estimated to be located,
    wherein, when the organ part is a small intestine, the processor is configured to:
    estimate which of a jejunum and an ileum the each of the one or more lesioned parts is located; and
    analyze the visibility of the each of the one or more lesioned parts based on the jejunum and the ileum that the each of the one or more lesioned parts is estimated to be located, and
    wherein, when the organ part is an esophagus, the processor is configured to:
    estimate which of a cervical esophagus, a thoracic esophagus, and an abdominal esophagus the each of the one or more lesioned parts is located; and
    analyze the visibility of the each of the one or more lesioned parts based on the cervical esophagus, the thoracic esophagus, and the abdominal esophagus that the each of the one or more lesioned parts is estimated to be located.

11. The image processing apparatus according to claim 1, wherein the processor is configured to:
    analyze a number of the one or more lesioned parts in the observation image; and
    analyze the visibility of the each of the one or more lesioned parts based on the number of the one or more lesioned parts analyzed.

12. The image processing apparatus according to claim 1, wherein the processor is configured to:
    set the display extension time to be a first length when it is determined that the visibility is higher than a predetermined threshold; and
    set the display extension time to be a second length longer than the first length when it is determined that the visibility is lower than the predetermined threshold.

13. The image processing apparatus according to claim 1, wherein the processor is configured to:
    analyze a type of the each of the one or more lesioned parts; and
    analyze the importance of the each of the one or more lesioned parts based on the type of the each of the one or more lesioned parts analyzed.

14. The image processing apparatus according to claim 1, wherein the processor is configured to:
    analyze malignancy of the each of the one or more lesioned parts; and
    analyze the importance of the each of the one or more lesioned parts based on the malignancy of the each of the one or more lesioned parts analyzed.

15. The image processing apparatus according to claim 1, wherein the processor is configured to:
    analyze an organ part,
    where the each of the one or more lesioned parts is located; and
    analyze the importance of the each of the one or more lesioned parts based on the organ part analyzed.

16. The image processing apparatus according to claim 15,
    wherein, when the organ part is a large intestine, the processor is configured to:
    estimate which of a rectum, a sigmoid colon, a descending colon, a left flexure of colon, a transverse colon, a right flexure of colon, an ascending colon, and a caecum the each of the one or more lesioned parts is located; and
    analyze the importance of the each of the one or more lesioned parts based on the rectum, the sigmoid colon, the descending colon, the left flexure of colon, the transverse colon, the right flexure of colon, the ascending colon and the caecum that the each of the one or more lesioned parts is estimated to be located,
    wherein, when the organ part is a stomach, the processor is configured to:

estimate which of a cardiac orifice, a stomach fundus, a gastric corpus, a gastric angle, a vestibule, a pyloric region, a pylorus, and a duodenum the each of the one or more lesioned parts is located; and analyze the importance of the each of the one or more lesioned parts based on the cardiac orifice, the stomach fundus, the gastric corpus, the gastric angle, the vestibule, the pyloric region, the pylorus and the duodenum that the each of the one or more lesioned parts is estimated to be located, wherein, when the organ part is a small intestine, the processor is configured to:

estimate which of whether the organ part is a jejunum and an ileum the each of the one or more lesioned parts is located; and analyze the importance of the each of the one or more lesioned parts based on the jejunum and the ileum that the each of the one or more lesioned parts is estimated to be located, and wherein, when the organ part is an esophagus, the processor is configured to:

estimate which of a cervical esophagus, a thoracic esophagus, and an abdominal esophagus the each of the one or more lesioned parts is located; and analyze the importance of the each of the one or more lesioned parts based on the cervical esophagus, the thoracic esophagus, and the abdominal esophagus that the each of the one or more lesioned parts is estimated to be located.

17. The image processing apparatus according to claim 1, wherein the processor is configured to:

analyzes a color and luminance of the each of the one or more lesioned parts; and analyze the importance of the each of the one or more lesioned parts based on the color and luminance of the each of the one or more lesioned parts analyzed.

18. The image processing apparatus according to claim 1, wherein the processor is configured to analyze the importance of the each of the one or more lesioned parts based on a shape and a size of the each of the one or more lesioned parts.

19. The image processing apparatus according to claim 18, wherein the processor is configured to analyze the importance based on the shape of the each of the each of the one or more lesioned parts.

20. The image processing apparatus according to claim 19, wherein, when an observation target organ part of the endoscope is a large intestine, the processor is configured to:

analyze which shape of sessile, sub-sessile, pedunculate, a superficial elevated type, a superficial flat type, and a superficial depressed type the shape of the each of the detected one or more lesioned parts is; and analyze the importance of the each of the one or more lesioned parts based on the shape of sessile, sub-sessile, pedunculate, the superficial elevated type, the superficial flat type, and the superficial depressed type the shape of the each of the one or more lesioned parts is analyzed to be, and wherein, when the observation target organ part is a stomach, the processor is configured to:

analyze which shape of a submucosal tumor type, a sessile type, a sub-sessile type, a pedunculate type, a superficial type, a tumorous type, an ulcerative and localized type, an infiltrative ulcerative type, and a diffuse infiltrative type the shape of the each of the one or more lesioned parts is; and analyze the importance of the each of the one or more lesioned parts based on the shape of the submucosal tumor type, the sessile type, the sub-sessile type, the pedunculate type, the superficial type, the tumorous type, the ulcerative and localized type, the infiltrative ulcerative type, and the diffuse infiltrative type the shape of the each of the one or more lesioned parts is analyzed to be.

21. The image processing apparatus according to claim 18, wherein the processor is configured to analyze the importance based on the size of the each of the one or more lesioned parts.

22. The image processing apparatus according to claim 1, wherein the processor is configured to:

set the display extension time to be a first length when it is determined that the importance is higher than a predetermined threshold; and set the display extension time to be a second length shorter than the first length when it is determined that the importance is lower than the predetermined threshold.

23. The image processing apparatus according to claim 1, wherein the processor is configured to analyze, as analysis of the visibility, at least one of a distance from the endoscope, an occupied area, a shape, a size, a position in the observation image, a color, luminance or an organ part.

24. The image processing apparatus according to claim 1, wherein the processor is configured to sequentially receive a plurality of the observation image.

25. The image processing apparatus according to claim 1, wherein the processor is configured to perform extension of the highlighting processing for the display extension time after detection of the one or more lesioned parts became impossible.

26. An image processing method comprising:

receiving an observation image obtained by picking up an image of an object with an endoscope;

detecting one or more lesioned parts, which each is an observation target of the endoscope, from the observation image;

performing highlighting processing on each of the one or more lesioned parts;

analyzing visibility of each of the one or more lesioned parts;

analyzing an importance of the each of the one or more lesioned parts;

setting a display extension time of the highlighting processing of each of the one or more lesioned parts according to the analyzed visibility and the analyzed importance; and outputting the observation image to which each of the one or more lesioned parts on which the highlighting processing has been performed is added.

27. A non-transitory computer-readable recording medium that stores a computer program, the computer program causing a computer to:

receive an observation image obtained by picking up an image of an object with an endoscope;

detect one or more lesioned parts, which each is an observation target of the endoscope, from the observation image;

perform highlighting processing on each of the one or more lesioned parts;
analyze visibility of each of the one or more lesioned parts;
analyze an importance of the each of the one or more lesioned parts;
set a display extension time of the highlighting processing of each of the one or more lesioned parts according to the analyzed visibility and the analyzed importance; and
output the observation image to which each of the one or more lesioned parts on which the highlighting processing has been performed is added.

* * * * *